(12) United States Patent
Reo et al.

(10) Patent No.: US 10,898,375 B2
(45) Date of Patent: Jan. 26, 2021

(54) PARANASAL SINUS ACCESS IMPLANT DEVICES AND RELATED PRODUCTS AND METHODS

(71) Applicant: SINOPSYS SURGICAL, INC., Boulder, CO (US)

(72) Inventors: Michael Lawrence Reo, Redwood City, CA (US); Brian James Willoughby, Denver, CO (US); Christopher Lee Oliver, Denver, CO (US); Harry Ross, Boulder, CO (US); Donald F. Schomer, Bellaire, TX (US)

(73) Assignee: Sinopsys Surgical, Inc., Boulder, CO (US)

( * ) Notice: Subject to any disclaimer, the term of this patent is extended or adjusted under 35 U.S.C. 154(b) by 699 days.

(21) Appl. No.: 15/328,388

(22) PCT Filed: Jul. 24, 2015

(86) PCT No.: PCT/US2015/042099
§ 371 (c)(1),
(2) Date: Jan. 23, 2017

(87) PCT Pub. No.: WO2016/015002
PCT Pub. Date: Jan. 28, 2016

(65) Prior Publication Data
US 2017/0216094 A1    Aug. 3, 2017

Related U.S. Application Data

(60) Provisional application No. 62/028,682, filed on Jul. 24, 2014.

(51) Int. Cl.
*A61F 9/007*    (2006.01)
*A61F 13/12*    (2006.01)
*A61M 27/00*    (2006.01)

(52) U.S. Cl.
CPC ........ *A61F 9/00772* (2013.01); *A61F 13/126* (2013.01); *A61M 27/002* (2013.01);
(Continued)

(58) Field of Classification Search
CPC .. A61F 9/00772; A61F 13/126; A61F 27/002; A61F 2240/001; A61F 2250/0025; A61M 2207/00; A61M 2209/06
See application file for complete search history.

(56) References Cited

U.S. PATENT DOCUMENTS 3,726,284 A    4/1973 Parker
3,948,272 A    4/1976 Guibor
(Continued)

FOREIGN PATENT DOCUMENTS

CN    2077268 U    5/1991
EP    0631793 A1    1/1995
(Continued)

OTHER PUBLICATIONS

Bagdonaite, Laura, M.D. et al. "Twelve-Year Experience of Lester Jones Tubes—Results and Comparison of 3 Different Tube Types", Opthalmic Plastic Reconstructive Surgery (2015) vol. 31, No. 5., pp. 352-356.
(Continued)

*Primary Examiner* — Philip R Wiest
(74) *Attorney, Agent, or Firm* — Snell & Wilmer L.L.P.

(57) ABSTRACT

A paranasal sinus access implant device may include one or more material or geometric features that may enhance performance of one or more portions of the implant device, for example an exposed surface including an antimicrobial agent. Various products and methods may include or use such an implant device.

4 Claims, 16 Drawing Sheets

(52) U.S. Cl.
CPC . *A61F 2240/001* (2013.01); *A61F 2250/0019* (2013.01); *A61F 2250/0025* (2013.01); *A61M 2207/00* (2013.01); *A61M 2209/06* (2013.01); *A61M 2210/0612* (2013.01); *A61M 2210/0681* (2013.01)

(56) References Cited

U.S. PATENT DOCUMENTS

| | | |
|---|---|---|
| 4,915,684 A | 4/1990 | MacKeen et al. |
| 4,921,485 A | 5/1990 | Griffiths |
| 5,169,386 A | 12/1992 | Becker et al. |
| 5,318,513 A | 6/1994 | Leib et al. |
| 5,345,948 A | 9/1994 | O'Donnell, Jr. |
| 6,041,785 A | 3/2000 | Webb |
| 6,083,188 A | 7/2000 | Becker |
| 6,113,567 A | 9/2000 | Becker |
| 6,629,533 B1 | 10/2003 | Webb et al. |
| 6,878,165 B2 | 4/2005 | Makino |
| 6,966,888 B2 | 11/2005 | Cullen et al. |
| 7,156,821 B2 | 1/2007 | Dohlman |
| 7,169,163 B2 | 1/2007 | Becker |
| 7,361,168 B2 | 4/2008 | Makower et al. |
| 7,410,480 B2 | 8/2008 | Muni et al. |
| 7,419,497 B2 | 9/2008 | Muni et al. |
| 7,462,175 B2 | 12/2008 | Chang et al. |
| 7,500,971 B2 | 3/2009 | Chang et al. |
| D590,935 S | 4/2009 | Becker |
| 7,547,323 B2 | 6/2009 | Lavigne |
| 7,559,925 B2 | 7/2009 | Goldfarb et al. |
| 7,641,644 B2 | 1/2010 | Chang et al. |
| 7,645,272 B2 | 1/2010 | Chang et al. |
| 7,654,997 B2 | 2/2010 | Makower et al. |
| 7,713,255 B2 | 5/2010 | Eaton et al. |
| 7,720,521 B2 | 5/2010 | Chang et al. |
| 7,727,186 B2 | 6/2010 | Makower et al. |
| 7,727,226 B2 | 6/2010 | Chang et al. |
| 7,758,534 B2 | 7/2010 | Pearson |
| 7,771,409 B2 | 8/2010 | Chang et al. |
| 7,785,315 B1 | 8/2010 | Muni et al. |
| 7,803,150 B2 | 9/2010 | Chang et al. |
| 7,846,124 B2 | 12/2010 | Becker |
| 9,022,967 B2 | 5/2015 | Oliver et al. |
| 9,308,358 B2 | 4/2016 | Oliver et al. |
| 9,561,350 B2 | 2/2017 | Ross et al. |
| 9,572,964 B2 | 2/2017 | Ross et al. |
| 9,700,459 B2 | 7/2017 | Willoughby et al. |
| 9,901,721 B2 | 2/2018 | Oliver et al. |
| 10,035,004 B2 | 7/2018 | Oliver et al. |
| 2002/0032444 A1 | 3/2002 | Mische |
| 2002/0107579 A1 | 8/2002 | Makino |
| 2004/0064150 A1 | 4/2004 | Becker |
| 2004/0077989 A1 | 4/2004 | Goode et al. |
| 2004/0116958 A1 | 6/2004 | Gopferich et al. |
| 2004/0204704 A1 | 10/2004 | Tamplenizza et al. |
| 2004/0254516 A1 | 12/2004 | Murray et al. |
| 2005/0197614 A1 | 9/2005 | Pritchard et al. |
| 2005/0240143 A1 | 10/2005 | Dohlman |
| 2005/0245906 A1 | 11/2005 | Makower et al. |
| 2005/0273033 A1 | 12/2005 | Grahn et al. |
| 2006/0063973 A1 | 3/2006 | Makower et al. |
| 2006/0142736 A1 | 6/2006 | Hissink et al. |
| 2006/0251575 A1 | 11/2006 | Morgenstern |
| 2006/0276738 A1 | 12/2006 | Becker |
| 2007/0005120 A1 | 1/2007 | Villacampa et al. |
| 2007/0112291 A1 | 5/2007 | Borgesen |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0208252 A1 | 9/2007 | Makower |
| 2007/0208301 A1 | 9/2007 | Evard et al. |
| 2007/0249896 A1 | 10/2007 | Goldfarb et al. |
| 2007/0255263 A1 | 11/2007 | Sugimoto |
| 2007/0269487 A1 | 11/2007 | De Juan et al. |
| 2007/0276314 A1 | 11/2007 | Becker |
| 2007/0282305 A1 | 12/2007 | Goldfarb et al. |
| 2007/0293726 A1 | 12/2007 | Goldfarb et al. |
| 2007/0293727 A1 | 12/2007 | Goldfarb et al. |
| 2008/0082037 A1 | 4/2008 | Pearson |
| 2008/0097154 A1 | 4/2008 | Makower et al. |
| 2008/0097354 A1 | 4/2008 | Lavigne |
| 2008/0097514 A1 | 4/2008 | Chang et al. |
| 2008/0103361 A1 | 5/2008 | Makower et al. |
| 2008/0103521 A1 | 5/2008 | Makower et al. |
| 2008/0119693 A1 | 5/2008 | Makower et al. |
| 2008/0125626 A1 | 5/2008 | Chang et al. |
| 2008/0125805 A1 | 5/2008 | Mische |
| 2008/0132938 A1 | 6/2008 | Chang et al. |
| 2008/0154237 A1 | 6/2008 | Chang et al. |
| 2008/0154250 A1 | 6/2008 | Makower et al. |
| 2008/0195041 A1 | 8/2008 | Goldfarb et al. |
| 2008/0228085 A1 | 9/2008 | Jenkins et al. |
| 2008/0234720 A1 | 9/2008 | Chang et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0306428 A1 | 12/2008 | Becker |
| 2008/0319424 A1 | 12/2008 | Muni et al. |
| 2009/0005763 A1 | 1/2009 | Makower et al. |
| 2009/0028923 A1 | 1/2009 | Muni et al. |
| 2009/0030274 A1 | 1/2009 | Goldfarb et al. |
| 2009/0036818 A1 | 2/2009 | Grahn et al. |
| 2009/0099626 A1 | 4/2009 | de Juan, Jr. et al. |
| 2009/0104248 A1 | 4/2009 | Rapacki et al. |
| 2009/0105749 A1 | 4/2009 | de Juan et al. |
| 2009/0187098 A1 | 7/2009 | Makower et al. |
| 2009/0198216 A1 | 8/2009 | Muni et al. |
| 2009/0204142 A1 | 8/2009 | Becker et al. |
| 2009/0221988 A1 | 9/2009 | Ressemann et al. |
| 2009/0240112 A1 | 9/2009 | Goldfarb et al. |
| 2009/0240237 A1 | 9/2009 | Goldfarb et al. |
| 2009/0275882 A1 | 11/2009 | Lavigne |
| 2009/0275903 A1 | 11/2009 | Lavigne |
| 2009/0281621 A1 | 11/2009 | Becker |
| 2009/0298390 A1* | 12/2009 | Rapacki ............ B24B 9/20 451/36 |
| 2009/0312745 A1 | 12/2009 | Goldfarb et al. |
| 2010/0034870 A1 | 2/2010 | Sim et al. |
| 2010/0042046 A1 | 2/2010 | Chang et al. |
| 2010/0076269 A1 | 3/2010 | Makower et al. |
| 2010/0099946 A1 | 4/2010 | Jenkins et al. |
| 2010/0100181 A1 | 4/2010 | Makower et al. |
| 2010/0106255 A1 | 4/2010 | Dubin |
| 2010/0114066 A1 | 5/2010 | Makower et al. |
| 2010/0121308 A1 | 5/2010 | Muni et al. |
| 2010/0174138 A1 | 7/2010 | Chang et al. |
| 2010/0174308 A1 | 7/2010 | Chang et al. |
| 2010/0198247 A1 | 8/2010 | Chang et al. |
| 2010/0210901 A1 | 8/2010 | Makower et al. |
| 2010/0241054 A1 | 9/2010 | Dacey, Jr. et al. |
| 2010/0268245 A1 | 10/2010 | Chang et al. |
| 2010/0274204 A1 | 10/2010 | Rapacki et al. |
| 2010/0274259 A1 | 10/2010 | Yaron et al. |
| 2010/0298862 A1 | 11/2010 | Chang et al. |
| 2010/0317969 A1 | 12/2010 | Becker |
| 2011/0004057 A1 | 1/2011 | Goldfarb et al. |
| 2011/0056852 A1 | 3/2011 | Frojd |
| 2011/0060214 A1 | 3/2011 | Makower |
| 2011/0105989 A1 | 5/2011 | Becker |
| 2011/0112512 A1 | 5/2011 | Muni et al. |
| 2011/0224680 A1 | 9/2011 | Barker |
| 2011/0276131 A1 | 11/2011 | De Juan, Jr. et al. |
| 2011/0311601 A1 | 12/2011 | Kleine et al. |
| 2012/0089071 A1* | 4/2012 | Oliver ............ A61F 9/00772 604/8 |
| 2012/0245539 A1 | 9/2012 | Zarins et al. |
| 2013/0030545 A1 | 1/2013 | Gross et al. |
| 2013/0231693 A1 | 9/2013 | Edgren et al. |
| 2013/0274647 A1 | 10/2013 | Oliver et al. |
| 2014/0012309 A1 | 1/2014 | Keith et al. |
| 2014/0120146 A1 | 5/2014 | Nakamura et al. |
| 2014/0135478 A1 | 5/2014 | Chaix et al. |
| 2014/0135916 A1 | 5/2014 | Clauson et al. |
| 2015/0065941 A1 | 3/2015 | Ross et al. |
| 2015/0157835 A1 | 6/2015 | Oliver et al. |

(56) References Cited

U.S. PATENT DOCUMENTS

| | | |
|---|---|---|
| 2015/0231376 A1 | 8/2015 | Willoughby et al. |
| 2016/0135992 A1 | 5/2016 | Schaller et al. |
| 2016/0250070 A1 | 9/2016 | Willoughby et al. |
| 2016/0271378 A1 | 9/2016 | Oliver et al. |
| 2017/0165108 A1 | 6/2017 | Bianchi et al. |
| 2017/0209678 A1 | 7/2017 | Willoughby et al. |
| 2018/0126131 A1 | 5/2018 | Oliver et al. |
| 2019/0015643 A1 | 1/2019 | Oliver et al. |

FOREIGN PATENT DOCUMENTS

| | | |
|---|---|---|
| FR | 2813522 A1 | 3/2002 |
| WO | 2001078631 A2 | 10/2001 |
| WO | 2005000154 A2 | 1/2005 |
| WO | 2006133066 A2 | 12/2006 |
| WO | 2007115259 A2 | 10/2007 |
| WO | 2008036671 A1 | 3/2008 |
| WO | 2008045242 A2 | 4/2008 |
| WO | 2009032328 A1 | 3/2009 |
| WO | 2009035562 A2 | 3/2009 |
| WO | 2009145755 A1 | 12/2009 |
| WO | 2010078145 A1 | 7/2010 |
| WO | 2010096822 A2 | 8/2010 |
| WO | 2010107826 A2 | 9/2010 |
| WO | 2010111528 A2 | 9/2010 |
| WO | 20110066479 A1 | 6/2011 |
| WO | 2012048278 A2 | 4/2012 |
| WO | 2013130468 A1 | 9/2013 |
| WO | 20130154843 A1 | 10/2013 |
| WO | 20140116980 A1 | 7/2014 |
| WO | 2015069433 A1 | 5/2015 |
| WO | 2016014996 A1 | 1/2016 |
| WO | 2016015002 A1 | 1/2016 |
| WO | 2017132573 A1 | 8/2017 |
| WO | 2019060605 A1 | 3/2019 |

OTHER PUBLICATIONS

Sadeghi, Nader, M.D. et al. Transnasal Endoscopic Medial Maxillectomy for Inverting Papilloma. Laryngoscope (2003) 113:749-753.

Mangan, BG et al. Bilateral Nasolacrimal Duct Atresia in a Cria. Veterinary Opthalmology (2008) 11, 1, 49-54.

Giuliano, EA et al. Dacryocystomaxillorhinostomy for Chronic Dacryocystitis in a Dog. Veterinary Opthalmology (2006) 9, 2, 89-94.

Wilson, DG et al. Surgical Reconstruction of the Nasolacrimal System in the Horse. Equine Veterinary Science (1991) vol. II, No. 4, pp. 232-234.

Steinmetz, A et al. Surgical Removal of a Dermoid Cyst From the Bony Part of Thenasolacrimal Duct in a Scottish Highland Cadle Heifer. Veterinary Opthalmology (2009) 12, 4, 259-262.

McIlnay, TR et al. Use of Canaliculorhinostomy for Repair of Nasolacrimal Duct Obstruction in a Horse. JAVMA (2001) vol. 218, No. 8. Scientific Reports: Clinical Report. 1323-1324.

Gionfriddo Jr. The nasolacrimal system. In: Textbook of Small Animal Surgery 3rd edition. 2003, Slatter OM ed. Saunders, Philadelphia PA, pp. 1356-1358.

Tang et al. "Influence of silicone surface roughness and hydrophobicity on adhesion and colonization of *Staphylococcus epidermidis*". Journal of Biomedical Materials Research. Part A (2008) vol. 88A, No. 2., pp. 454-463.

\* cited by examiner

DETAIL B

DETAIL A

PARANASAL SINUS ACCESS IMPLANT DEVICES AND RELATED PRODUCTS AND METHODS

CROSS-REFERENCE TO RELATED APPLICATIONS

This application claims the benefit of U.S. provisional patent application No. 62/028,682 entitled "APPARATUSES, TOOLS, KITS AND METHODS RELATING TO PARANASAL SINUS ACCESS" filed Jul. 24, 2014, each and every portion of which is incorporated herein by reference.

This application incorporates by reference each and every portion of the following: international patent application no. PCT/US2011/055456 entitled "IMPLANT DEVICE, TOOL, AND METHODS RELATING TO TREATMENT OF PARANASAL SINUSES" filed Oct. 7, 2011; U.S. nonprovisional patent application Ser. No. 13/225,213 entitled "IMPLANT DEVICE, TOOL, AND METHODS RELATING TO TREATMENT OF PARANASAL SINUSES" filed Sep. 2, 2011; U.S. provisional patent application No. 61/528,058 entitled "IMPLANT DEVICE, TOOL, AND METHODS RELATING TO TREATMENT OF PARANASAL SINUSES" filed Aug. 26, 2011; U.S. provisional patent application No. 61/404,716 entitled "METHODS AND TOOLS FOR TREATMENT AND PREVENTION OF SINUSITIS" filed Oct. 8, 2010; U.S. provisional patent application No. 61/623,022 entitled "IMPLANTATION TOOLS, TOOL ASSEMBLIES, KITS AND METHODS" filed Apr. 11, 2012; international patent application no. PCT/US2013/034475 entitled "IMPLANTATION TOOLS, TOOL ASSEMBLIES, KITS AND METHODS" filed Mar. 28, 2013; U.S. provisional patent application No. 61/757,046 entitled "IMPLANT DEVICE, METHOD AND KIT FOR IMPLANTATION BETWEEN THE LACRIMAL SYSTEM AND A PARANASAL SINUS" filed Jan. 25, 2013; U.S. provisional patent application No. 61/891,250 entitled "PARANASAL SINUS ACCESS IMPLANT DEVICES AND RELATED TOOLS, METHODS AND KITS" filed Oct. 15, 2013; international patent application no. PCT/US2014/012995 entitled "PARANASAL SINUS ACCESS IMPLANT DEVICES AND RELATED TOOLS, METHODS AND KITS" filed Jan. 24, 2014; U.S. provisional patent application No. 61/891,710 entitled "APPARATUSES, TOOLS, KITS AND METHODS RELATING TO FLUID MANIPULATION TREATMENTS OF PARANASAL SINUSES" filed Oct. 16, 2013; and international patent application no. PCT/US2014/060891 entitled "APPARATUS, TOOLS AND KITS RELATING TO FLUID MANIPULATION TREATMENTS OF PARANASAL SINUSES" filed Oct. 16, 2014.

This application incorporates by reference each and every portion of contemporaneously filed international patent application no. PCT/US2015/042089 entitled "APPARATUSES, TOOL, KITS AND METHODS RELATING TO PARANASAL SINUS ACCESS".

FIELD OF THE INVENTION

The invention relates to treatment of conditions of the paranasal sinuses, including with respect to paranasal sinus access implant devices and products and methods including paranasal access implant devices.

BACKGROUND OF THE INVENTION

In the United States alone, 35 million people a year are treated for sinus infections, or sinusitis, and 7 million of those will suffer from chronic sinusitis and will have minimal response to prescription drug therapies. Conventional surgical interventions may be expected to, at best, offer only moderate symptomatic improvement but no cure.

Current drug therapies include oral administration as pills and nasal topical administration, neither of which is conducive to delivering adequate concentration of medication to the involved paranasal sinus. In addition to medication, frequent sinus irrigation can be helpful in flushing out debris and irritants, promoting ciliary function and obstructing viscous fluids, but patients are generally not able to adequately perform this procedure at home.

For patients with particularly severe symptoms, surgical drainage has been an option of last resort. An early surgical procedure was the Caldwell-Luc procedure, which involves creating a permanent fistula from the base of the maxillary sinus into the oral cavity by way of an incision into the canine fossa above the front upper canine teeth. More recently, other surgical access points to the paranasal sinuses have been attempted. A variety of endoscopic techniques have been developed that access the paranasal sinuses through the nose, including functional endoscopic sinus surgery (FESS) and balloon sinuplasty. All attempt to increase drainage or promote irrigation, but utilize different routes or tools. Implantation of an implant device through such a surgically-formed fistula between the lacrimal apparatus and a paranasal sinus has been identified as a technique to provide direct access to the paranasal sinus, and through which a variety of medical treatments and medical procedures may be directed to the paranasal sinus. Though these surgical approaches are widely recognized, millions of patients continue to suffer long-term disability and discomfort. There continues to be a need for effective and convenient techniques to administer drugs directed to treatment of conditions of the paranasal sinuses.

SUMMARY OF INVENTION

Paranasal sinus access implant devices may be configured to be implanted in a human to provide fluid access to a paranasal sinus through an internal passage of such a paranasal sinus access implant device, with the internal passage being accessible through an opening in a head of the paranasal sinus access implant device. The head may be configured to be disposed in the lacrimal apparatus in the orbit, for example between the medial canthus and the medial side of the adjacent eyeball, when the paranasal sinus access implant device is implanted to provide fluid access to a paranasal sinus. Such paranasal sinus access implant devices have significant potential for performance of medical procedures and treatments of paranasal sinuses, but such potential has not yet been realized. Treatment compositions may be delivered to a paranasal sinus through such an implant device by administering eye drops that may then flow through the implant device to a paranasal sinus. Fluid administrations may also be made by inserting a needle through the implant device to inject fluid directly into the paranasal sinus and medical procedures may involve passing a medical device through the implant device and into the paranasal sinus. However, use of such implant devices face challenges, including in relation to ease of implantation and control over the implantation procedure, patient comfort in relation to implanted devices and susceptibility of exposed surfaces of implant device to formation of biofilms following implantation. Also, mechanical interactions with the implant device following implantation, for example to perform a medical procedure through the implant device, have potential to structurally damage the implant device or to dislodge the implant device or disrupt the anchoring of the implant device in surrounding tissue. There are continued needs for implant devices and related procedures to address these challenges. Various aspects of this disclosure relate to implant device designs, methods and products that may address to some degree one or more of such needs.

A first aspect of the disclosure involves a paranasal sinus access implant device useful for implantation in a human to fluidly connect a lacrimal apparatus to a paranasal sinus through a fistula formed between the lacrimal apparatus and the paranasal sinus. Such a paranasal sinus access implant device may comprise:

a proximal end at a first longitudinal end of the implant device to be disposed in the lacrimal apparatus when the implant device is implanted and a distal end at a second longitudinal end of the implant device to be disposed in the paranasal sinus when the implant device is implanted;

a length longitudinally along the implant device between the proximal end and the distal end in a range of from 2 millimeters to 50 millimeters.

a conduit, located between the proximal end and distal end, to be disposed through a fistula between the lacrimal apparatus and the paranasal sinus when the implant device is implanted;

a head located proximal of the conduit, to be disposed in the lacrimal apparatus when the implant device is implanted; and an internal passage through the head and the conduit, to provide a fluid communication path between the lacrimal apparatus and the paranasal sinus when the implant device is implanted, the internal passage having a width through at least a portion of the conduit in a range of from 0.25 millimeter to 5 millimeters.

The paranasal sinus access implant device may include one or more material or geometry features, or be associated with one or more material, to at least partially address one of more of the needs noted above. The paranasal sinus access implant device may include at least one (any one, any combination of more than one or all) of the following features:

(i) the conduit comprises a first material having a first hardness and the head comprises a second material having a second hardness that is smaller than the first hardness;

(ii) the conduit comprises a distal portion to be disposed in the paranasal sinus when the implant device is implanted, the distal portion of the conduit comprising a structural portion of a first material having a first hardness and a skin portion supported by the structural portion, the skin portion including a second material having a second hardness that is smaller than the first hardness;

(iii) the head comprises a structural portion of a first material having a first hardness and a skin portion supported by the structural portion, the skin portion including a second material having a second hardness that is smaller than the first hardness;

(iv) the head has an exposed surface of a second material having a hardness of not larger than Shore A 45 durometer;

(v) the head comprises an exposed surface of a second material, the exposed surface having an average roughness (Ra) of not larger than 200 nanometers;

(vi) the conduit comprises a distal portion to be disposed in the paranasal sinus when the implant device is implanted, the distal portion of the conduit comprising an exposed surface of a second material, the exposed surface having an average roughness (Ra) of not larger than 200 nanometers;

(vii) the head comprises an exposed surface of a second material comprising a wetting agent to impart hydrophilicity to the exposed surface;

(viii) the conduit comprises a distal portion to be disposed in the paranasal sinus when the implant device is implanted, the distal portion of the conduit comprising an exposed surface of a second material comprising a wetting agent to impart hydrophilicity to the exposed surface;

(ix) the head comprises an exposed surface of a second material comprising an antimicrobial agent;

(x) the conduit comprises a distal portion to be disposed in the paranasal sinus when the implant device is implanted, the distal portion of the conduit comprising an exposed surface of a second material comprising an antimicrobial agent;

(xi) the head comprises a distal side having a concave surface disposed toward the distal end of the implant device;

(xii) the internal passage has a surface of a second material comprising a lubricity agent;

(xiii) at least a portion of the conduit is of a radiopaque material;

(xiv) the internal passage has a surface geometry comprising rifling;

(xv) the conduit comprises a distal extension portion that is extendable and contractible to lengthen and shorten a longitudinal length of a distal portion of the conduit disposed in the paranasal sinus when the implant device is implanted; and (xvi) the implant device is packaged in sterile packaging in contact with a storage liquid.

Several of these features (i)-(xvi) involve use of a "second material", which is a term used for convenience of reference and description and does not indicate a distinction from another material that may be used in the implant device, except as specifically identified as such. Reference to a second material is often to a material that may be selectively used to enhance a selected portion of the implant device, rather than as a main structural material of construction for the implant device or a portion of the implant device. Such a main structural material may sometimes be referred to herein for convenience as a "first material". An implant device may include more than one such "second material" and may include one or more than one such "first material". A material (e.g., "first material" or "second material") that is exposed at a surface of an implant device may be referred to interchangeably as an "exposed material".

Another aspect of the disclosure involves a method of making a paranasal sinus access implant device of the first aspect that includes at least one such second material. The method comprises: providing a preliminary form including a preliminary head structure and a preliminary conduit structure; and forming at least one said second material supported by one or both of the preliminary head structure and the preliminary conduit structure. The implant device may be according to the first aspect and may include at least one second material, for example as noted in any one of features (i)-(x) of the first aspect. A resulting structure may be used as a final paranasal sinus access implant device product or may be used as new preliminary form for further processing in preparation of a final implant device product.

Another aspect of the disclosure involves a method for performing a medical procedure in relation to a paranasal sinus and/or administering a treatment composition or performing a medical operation through an implanted implant device directed to the paranasal sinus.

Another aspect of the disclosure involves a paranasal sinus access implant device packaged in sterile packaging in contact with a sterile storage liquid. The product may include a paranasal sinus access implant device, sterile storage liquid and sterile packaging, wherein the implant device and the storage liquid are disposed within the sterile packaging. In another aspect of the disclosure, a method for implanting a paranasal sinus access implant device to fluidly connect a lacrimal apparatus and a paranasal sinus may include removing such an implant device from the sterile packaging of such a product, and implanting the implant device with a proximal end disposed in the lacrimal apparatus and a distal end disposed in the paranasal sinus to fluidly connect the lacrimal apparatus and the paranasal sinus through an internal passage of the implant device.

A number of feature refinements and additional features are applicable to any one or more of these or other aspects of the disclosure. These feature refinements and additional features may be used individually or in any combination within the subject matter of any such aspects. As such, each of the following features may be, but are not required to be, used with any other feature or combination of features in relation to the same aspect or any other aspect of the disclosure.

For brevity, paranasal sinus access implant devices are referred to herein as simply implant devices.

Various feature refinements and additional features are applicable to the paranasal sinus access implant device.

In relation to any of features (i)-(iii), in some implementations the first material may often have a hardness of at least Shore A 50 durometer, at least Shore A 55 durometer, at least Shore A 60 durometer, at least Shore A 65 durometer, at least Shore A 70 durometer or at least Shore A 75 durometer. Such a first material may often have a hardness not greater than Shore A 100 durometer, not greater than Shore A 95 durometer, not greater than Shore A 90 durometer, not greater than Shore A 85 durometer or not greater than Shore A 80 durometer. Such a first material may comprise, for example, silicone materials, polyurethane materials, silicone-urethane copolymers, silicone-polycarbonate copolymers, polycarbonate-urethane copolymers and silicone-polycarbonate-urethane copolymers. Such first material may be a structural material of construction for the implant device or a portion thereof. One preferred silicone material for many implementations includes polydimethylsiloxane as a primary silicone polymer component. In some preferred implementations, the first material has a hardness that is larger than the hardness of the second material by at least 10, at least 15, at least 20, at least 25 or at least 30 Shore A durometer units.

In relation to any one of features (i)-(x), a second material may in some implementations have a hardness that is not larger than Shore A 45 durometer, not larger than Shore A 40 durometer, not larger than Shore A 35 durometer, not larger than Shore A 30 durometer, not larger than Shore A 25 durometer or not larger than Shore A 20 durometer. In some implementations a second material may have a hardness of at least Shore A 5 durometer or at least Shore A 10 durometer. One preferred material for use in a second material to form a softer layer over a harder structural material is a silicone-based material, which may be a silicone polymer material or a silicone hydrogel material. In relation to features (ii) and (iii), such a skin portion with a softer second material may be in a layer having a thickness of at least 2 microns, at least 5 microns, or at least 10 microns, or at least 20 microns, and often having a thickness of not larger than 200 microns, not larger than 100 microns, not larger than 50 microns, not larger than 25 microns, not larger than 20 microns or not larger than 15 microns. Such a skin portion may have an exposed surface on the implant device (e.g., on the outside of the head or conduit or on walls of the internal passage), or may be covered by a further layer of material, for example of a wetting agent or antimicrobial agent. Silicone hydrogel materials may be silicone hydrogels such as are used in contact lenses. Such silicone hydrogels may include hydrophilic functionality to counteract hydrophobicity of polysiloxanes. Such hydrophilic functionality may be provided for example, by one or more materials such as pyrrolidone-based functionality (e.g., incorporation of N-vinylpyrrolidone or polyvinylpyrrolidone (PVP), also referred to as poly-N-vinylpyrrolidone or as poly-N-vinyl-2-pyrrolidone, acrylamide-based functionality (e.g. dimethyl acrylamide functionality), glycol-based functionality (e.g., polyethylene glycol) and/or TRIS-based functionality. Some example commercial silicone hydrogel material products include balafilcon A (Bausch & Lomb), lotrafilcon A (CIBA Vision), lotrafilcon B (CIBA Vision), comfilcon A (CooperVision), senofilcon A (Johnson & Johnson Vision Care) and galyfilcon A (Johnson & Johnson Vision Care).

In relation to either one of features (v) or (vi), such an exposed surface may have an average roughness (Ra) of not larger than 200 nanometers, not larger than 100 nanometers, not larger than 50 nanometers, not larger than 35 nanometers, not larger than 25 nanometers, not larger than 20 nanometers, not larger than 15 nanometers or not larger than 10 nanometers. Such an average roughness (Ra) may often be at least 1 nanometer, or at least 2 nanometers or at least 5 nanometers. Average roughness Ra may be determined by any suitable analytical technique. Average roughness (Ra) may be as determined by optical non-contact profilometry, laser profilometry or atomic force microscopy (AFM). In preferred implementations, the Average roughness (Ra) is as determined by optical non-contact profilometry.

In relation to either one of features (vii) or (viii), such a wetting agent may be any polymeric or non-polymeric material that imparts increased hydrophilicity to the exposed surface relative to material of the implant device not including such a wetting agent. Such a wetting agent may be immobile (e.g., through cross-linking or polymer functionalization) or may elute over time (e.g., deposited surface coating or leachable component mixed into material composition). The wetting agent may be or include one or more surfactants. Multiple wetting agents may be used together. A wetting agent may include multiple components that together provide desired wettability. Some example wetting agents include polyvinylpyrrolidone (PVP), polyethylene glycol (PEG), polyethylene oxide, polypropylene oxide, poly(oxyethylene)-poly(oxybutylene) copolymers, hydroxypropylmethylcelluluse (HPMC), polyvinyl alcohol (PVA), poloxamines and hyaluronic acid. The wetting agent may be applied as a coating, alone or mixed with another material, may be part of a material of construction, or may be bonded to the surface of the implant device. For example, polyethylene glycol may be grafted onto silicone elastomers, such as by atmospheric pressure plasma induced grafting. As another example, polyethylene glycol may be copolymerized with some silicone materials (e.g., with polydimethyl siloxane). As other examples, any of these example materials could be deposited on a surface as a coating. A wetting agent may be a part of a silicone hydrogel composition at the exposed surface.

In relation to either one of features (ix) or (x), such an antimicrobial agent may be any material that has antimicrobial properties (e.g., kills or inhibits growth of or interaction with microorganisms), which may significantly help to prevent formation of biofilms on such exposed surfaces having the antimicrobial agent. Such an antimicrobial agent may, for example, be of a type as have been described for use with catheters and/or contact lenses. Such an antimicrobial agent may be immobile (e.g., through covalent or strong ionic attachment) or may elute over time (e.g., deposited surface coating or leachable component mixed into material composition). Multiple antimicrobial agents may be used together. An antimicrobial agent may include multiple components that together provide antimicrobial activity. An antimicrobial agent may be incorporated into or applied to a polymer composition of the implant device that is exposed at an exterior surface of the implant device and/or that is exposed at a surface of the walls of the internal passage. An antimicrobial may be incorporated into a material prior to using the material to fabricate an implant device or a preliminary form for an implant device, or may be incorporated into the material following formation of a preliminary form. An antimicrobial agent may be intermixed with other components, may be in the form of an adhered coating or may be covalently or otherwise attached to a polymeric material (e.g., polysiloxane) or other material of the implant device. Some example antimicrobial agents include silver (including for example in the form of silver metal or silver salts and silver oxides), poly(ethylene oxide) (PEO), PEG and antimicrobial peptides. In some implementations, antimicrobial peptides are preferred. Some other example antimicrobial agents include chlorhexidine and/or silver sulfadiazine impregnation, minocycline-rifampicin impregnation, silver-containing nanoparticles impregnation, antimicrobial peptide impregnation or ionic or covalent incorporation (e.g., small cationic peptides, such as for example beta defensins, indolicidin, cecropin A, and magainins, melinines, protattins and lactoferrins). Some other examples of antimicrobial agents and methods and agents of attachment or adhesion may be found, for example, in the following publications, the entire contents of which are incorporated herein by reference:

Sousa, Cláudia et al., Mini-Review: Antimicrobial central venous catheters—recent advances and strategies, Biofouling, Vol. 27, No. 6, 609-620, July 2011.

Danese, Paul N, Antibiofilm Approaches: Prevention of Catheter Colonization, Chemistry & Biology, Vol. 9, 873-880, August 2002.

Gu, Xiaobo et al., Optimization of Ceragenins for Prevention of Bacterial Colonization of Hydrogel Contact lenses, IOVS, Vol. 54, No. 9, 6217-6223, September 2013, The Association for Research in Vision and Ophthalmology, Inc., www.iovs.org.

Sambhy, Vaun et al., Silver Bromide Nanoparticle/Polymer Composites: Dual Action Tunable Antimicrobial Materials, J. Am. Chem. Soc., Vol. 128, No. 30, 9798-9808, 2006.

Li X, et al., Antimicrobial functionalization of silicone surfaces with engineered short peptides having broad spectrum antimicrobial and salt-resistant properties, Acta Biomaterialia, Vol. 10, Issue 1, 258-266, January 2014.

Mishra, Biwajit et al., Site specific immobilization of a potent antimicrobial peptide onto silicone catheters: evaluation against urinary tract infection pathogens, J. Mater. Chem. B, Vol. 2, 1706-1716, 2014.

Cole, Nerida et al., In Vivo Performance of Melimine as an Antimicrobial Coating for Contact Lenses in Models of CLARE and CLPU, IOVS, Vol. 51, No. 1, 390-395, January 2010.

Balaban, Naomi et al., Prevention of *Staphylococcus aureus* biofilm on dialysis catheters and adherence to human cells, Kidney International, Vol. 63, 340-345, 2003.

U.S. Pat. No. 7,282,214.

U.S. Patent Application Publication 2002/0068013.

Antimicrobial peptides may be deposited on a surface by themselves, or in a mixture with another material (e.g., polymeric material) that helps to immobilize the antimicrobial peptide at the exposed surface. For example, such an antimicrobial agent may be mixed with a polymeric material that helps to immobilize the antimicrobial agent. Such a polymeric material may be a wetting agent, for example any of the polymeric wetting agents listed previously. In some preferred alternatives, an antimicrobial peptide may be covalently attached to a polymeric material, for example to silicone materials, according to known methods. Such antimicrobial peptides may be bonded directly to exposed material of a preliminary implant device form or may be pre-bonded to a polymer that is then deposited over surfaces of such a preliminary implant device form. Such covalent bonding, or attachment, may be through the use of one or more coupling agents. Coupling agents may be used to provide a stable bond improving affinity and adhesion between dissimilar materials (e.g., between a polymeric material of the implant device and an antimicrobial peptide or other antimicrobial agent). Coupling agents may be organic, inorganic and organic-inorganic. Some example organic coupling agents include isocyanates, anhydrides, amides, imides, acrylates, chlorotriazines, epoxides and organic acids, and various monomers, polymers and copolymers. Some example inorganic coupling agents include silicates. Some example organic-inorganic coupling agents include silanes and titanates. Silanes are one preferred group of coupling agents for covalent bonding to silicone and silicone hydrogel materials. In the case of polyethylene oxide as an antimicrobial agent, the polymer may be deposited over an exposed surface of a preliminary implant device form, or may be covalently attached to silicone or silicone hydrogel surfaces.

When an implant device includes an exposed surface of a second material, such as in any of features (iv)-(x), such an exposed surface may be in the form of a continuous or discontinuous surface feature. By a continuous surface feature it is meant a contiguous surface area of homogeneous surface properties. By a discontinuous surface feature it is meant a surface area that includes multiple distinct surface areas with different surface properties, such as distinct domains of a surface property (e.g, surface spots of wetting agent, antimicrobial agent, etc.) separated by surface areas having a different surface property (e.g., not including the wetting agent, antimicrobial agent, etc. that is present in the spots). The exposed surface, whether continuous or discontinuous, may have an area of at least 1 square millimeter, at least 2 square millimeters, at least 3 square millimeters, 5 square millimeters, at least 10 square millimeters, at least 20 square millimeters, at least 50 square millimeters or at least 100 square millimeters. By area of a discontinuous exposed surface it is meant the entire area of exposed surface including all surface phases within the area perimeter to which the distinct domains (e.g., surface spots) extend. In some preferred implementations the exposed surface is in the form of a continuous surface feature. When an exposed surface of a second material is on an exterior distal portion of the conduit, such as in any of features (vi), (viii) or (x), the exposed surface may extend for at least 2 millimeters, at least 3 millimeters or at least 5 millimeters or at least 10 millimeters along a longitudinal length of the conduit or even over the entire length or essentially the entire length of the conduit.

An exposed surface of a second material on the head of an implant device may be disposed toward and/or away from tissue adjacent the fistula (e.g., toward or away from conjunctiva in the orbit) when the implant device is implanted. An exposed surface of a second material on the head may extend over all or essentially all of the exterior of the head. An exposed surface of a second material on the conduit may extend entirely or essentially entirely around an exterior circumference of at least a portion of the conduit, and may extend over all or essentially all of the exterior of the conduit, including portions of the conduit disposed in the fistula when implanted. An exposed surface of a second material may extend over a portion, all or essentially all of the walls of the internal passage of the implant device.

In some implementations, a single component may provide multiple effects, or multiple components together may provide multiple effects. For example a single component, or multiple components together, may serve as both a wetting agent and an antimicrobial agent.

In relation to any one of features (i)-(iii), there may be a plurality of layers that grade from harder to softer toward the surface of the implant device. For example, one or more additional material layer may be disposed between the first material and the second material, wherein the intermediate material has a hardness intermediate between the hardness of the first material and the hardness of the second material. For example, a material may be disposed between the first material and the second material that has such an intermediate hardness that is at least 10 Shore A durometer units smaller than the hardness of the first material and at least 10 Shore A durometer units larger than the hardness of the second material. Such an intermediate material may have a hardness in a range having a lower limit of Shore A 10 durometer, Shore A 15 durometer, Shore A 20 durometer or Shore A 25 durometer and an upper limit of Shore A 50 durometer, Shore A 45 durometer, Shore A 40 durometer or Shore A 35 durometer. Such an intermediate material may in some preferred implementations be a silicone material.

In relation to feature (xii), the lubricity agent may be any material that provides enhanced lubricity to such a surface of the internal passage. Some example lubricity agents include flurosilicone materials, very smooth silicone films and poly (p-xylylene) polymers. Flurosilicone materials include siloxane-based polymers including one of more fluoro groups. One example flurosilicone that may be used as a lubricity agent is the copolymer dimethyl methyl trifluoropropylsiloxane. An example of a material for a very smooth silicone film providing lubricity is a film made from silane-based materials such as ethyltriacetoxysilane. Some example poly (p-xylylene) polymers for providing lubricity include Parylene N or Parylene C polymer products (Para Tech Coating, Inc.). A coating of or including such a lubricity material may be formed on walls of the internal passage by any suitable technique, such as deposition from a solution or slurry followed by drying and curing as needed. Poly(p-xylylene) polymers may be deposited, for example, by chemical vapor deposition. Such a coating of or containing a lubricity agent may have any desired thickness to provide the desired level of lubricity. Such a coating may often have a thickness in a range having a lower limit of 1 micron, 2 microns, 5 microns or 10 microns and an upper limit of 200 microns, 100 microns, 50 microns, 25 microns or 15 microns.

With respect to feature (xiii) the radiopaque material may be in the form of a radiopaque additive or the radiopaque material may comprise a polymeric material that may have mixed therein a radiopaque additive, for example a particulate filler having a high radiopacity, also referred to as radiodensity. Examples of some radiopaque additives that may be used as or to impart radiopacity to a material include one or more of barium sulfate, titanium metal, tantalum metal, gold metal, platinum metal, iodine, bismuth subcarbonate, bismuth trioxide, bismuth oxychloride and tungsten. Some other radiopaque additives may be in the form metal beads or metal wires (e.g., of any of the metals listed above) embedded in a polymer matrix material. Such radiopaque additives may be added into a resin composition as a solid particulate filler, or may be present in solution in an initial composition with the radiopaque material then precipitating during manufacture processing. The radiopaque material may have any desired amount of the radiopaque additive to provide a desired level of radiopacity to the material, which will depend in part on the radiodensity properties of the particular radiopaque additive. In many implementations, the radiopaque additive may be present in the radiopaque material in an amount in a range having a lower limit of 1 weight %, 5 weight %, 10 weight %, 15 weight % or 20 weight % and an upper limit of 90 weight %, 80 weight %, 70 weight %, 60 weight %, 50 weight % or 40 weight %. The radiopaque material may include one or more polymeric components in addition to the radiopaque additive. Such polymeric components may be any of the polymeric materials described herein for making any portion of the implant device. In some implementations, the polymeric material will include a silicone material. In various implementations, at least a portion of the conduit including the radiopaque material may have a radiodensity of at least 50 Hounsfield units, at least 100 Hounsfield units, at least 200 Hounsfield units, at least 300 Hounsfield units or at least 400 Hounsfield units. Such radiodensity may in various implementations often be not larger than 1000 Hounsfield units, not larger than 900 Hounsfield units, not larger than 800 Hounsfield units or not larger than 700 Hounsfield units. In some preferred implementations, a radiopaque portion of the conduit extends for at least 2 millimeters, at least 3 millimeters, at least 4 millimeters, at least 5 millimeters, or at least 6 millimeters along a longitudinal length of the conduit. In some implementations, the radiopaque portion of the conduit may include at least such a portion of the longitudinal length of the conduit that includes a distal end of the conduit. Such a radiopaque portion may have a proximal end toward the head that is at least 0.5 millimeter, at least 1 millimeter, at least 2 millimeters or at least 3 millimeters distal of the head. In some implementations, the entire conduit may be made of radiopaque material. In other implementations, the head of the implant device may also be made of radiopaque material. However, in some preferred implementations at least a portion of the head, and more preferably substantially all of the flanged portions of the head, and even more preferably substantially all of the head, has a radiodensity that is smaller than the radiodensity of the radiopaque portion of the conduit, and which may often be a radiodensity of no larger than 75 Hounsfield units, no larger than 60 Hounsfield units, no larger than 40 Hounsfield units, no larger than 30 Hounsfield units or no larger than 20 Hounsfield units. In some particularly preferred implementations, the head does not contain a radiopaque additive. Having a radiopaque conduit portion permits easy radio imaging of that portion of the conduit during an implantation procedure to ensure proper positioning of the conduit for implantation and/or for long-term monitoring of the positioning of that portion of the conduit following implantation, for example to detect possible migration of the implant device post implantation. Having a substantially transparent or translucent head (preferably having both high radiotransparency and high transparency to visible light) makes the implant device less visible (e.g., in the orbit) and therefore more aesthetically pleasing to patients when implanted. At least a portion of the head, and preferably at least flanged portions of the head, may be visible light translucent or even visible light transparent. At least a portion of the head, and preferably at least flanged portions of the head may have a refractive index of not larger than 1.5, not larger than 1.45, not larger than 1.4 or not larger than 1.35. The refractive index may often be at least 1.3.

With respect to feature (xiv), the rifling may include a spiraling groove, recess, or other surface geometry in a wall of the internal passage, and may extend down a portion or all of the longitudinal length of the internal passage.

With respect to feature (xv), the extension portion may include or be a pleated or accordion-like structure that extends and contracts.

With respect to feature (xvi), the sterile packaging, implant device and storage liquid may be, for example, as described for the packaged product aspect of the disclosure.

Various feature refinements and additional features are applicable to a method for making a paranasal sinus access implant device.

A method for making a paranasal sinus access implant device may include forming such a second material over at least a portion of a preliminary head structure, over at least a portion of a preliminary conduit structure or over at least a portion of a preliminary internal passage structure. The second material may be formed over an existing first material or a previously provided second material, so that an implant device structure may include multiple second materials with one second material disposed over a prior second material. Forming a second material may include modifying the properties of an existing material of a preliminary structure, such as by impregnating an existing material with an additive or reacting an additive at the surface of an existing material. Second materials formed during final processing to prepare a final implant product may be exposed at a surface of the implant device product to provide a particular property for the implant device, for example a very smooth surface, hydrophilicity and/or antimicrobial activity. In some implementations, providing a preliminary form for use in the method may include modifying a prior preliminary form. In some implementations, providing a preliminary form may include molding a polymeric composition in the shape of the preliminary form, which may include curing a resin composition. Such molding techniques may include injection molding, compression molding and transfer molding. Such molding may be performed on an existing structure, such as an extruded tubular shaft forming a base structure for an implant device. Other features of an implant device (e.g., head and anchor protrusions) may be molded around the extruded form. The providing a preliminary form on which a second material may be formed may include removing flash from a molded article to provide a smoother surface on which to apply a second material. Forming a second material may include any deposition or impregnation technique. Some example techniques include dip molding or spray molding to apply a thin layer of a second material. Such dip molding or spray molding may include applying a precursor solution with at least one precursor for the second material, drying the precursor solution to leave residual precursor on the preliminary form and optionally curing as necessary residual precursor to form a final polymeric composition of the second material. In some implementations, a polymeric composition of the second material may include a thermoset polymer, and the curing may include heating precursor on the preliminary form to cure the thermoset composition. During drying, the implant device form may be subjected to three dimensional spinning to promote even distribution of deposited material on surfaces of the preliminary implant device on which the material is deposited. The forming a second material may include first forming an intermittent material over a desired portion of an implant device structure and then forming a second material over at least a portion of the preliminary material. The preliminary material may also be a second material, which may be the same or different than the subsequently applied second material. Forming a second material may include forming a preliminary material over a desired portion of the preliminary implant device form and then modifying the preliminary material to form the composition of the desired second material. For example, such modifying may include adding an additive material (e.g., antimicrobial agent, wetting agent, lubricity agent) to the preliminary material.

Various other feature refinements and additional features are applicable to the paranasal sinus access device of the first aspect.

The implant device may be configured to be implanted between the lacrimal apparatus in the orbit and a paranasal sinus (e.g., ethmoid sinus, frontal sinus or maxillary sinus), wherein when so implanted the proximal end is disposed in the lacrimal apparatus within the orbit and the distal end is disposed in the paranasal sinus.

The conduit may be configured so that an exterior of the conduit comprises an anchoring surface feature that assists to anchor the implant device when the implant device is implanted. The anchoring surface feature includes protrusion areas and recess areas. The second minimum wall thickness may occur at a location corresponding with at least one of the recess areas. The implant device may be configured so that when implanted the conduit is disposed through the fistula with at least a portion of the recess areas disposed within the fistula and with at least a portion of the protrusion areas disposed in the fistula and engaging tissue exposed within the fistula to anchor the implant device. The structural and mechanical characteristics of protrusion occurrences in the protrusion areas may affect anchoring performance of the protrusion areas. The height of the protrusion areas relative to the recess areas may affect anchoring effectiveness when the implant device is implanted. A larger height may provide greater anchor effectiveness, but also may involve a larger overall width of the implant device that must be inserted into the fistula. The protrusion areas may have a height relative to the recess areas of at least 0.1 millimeter, at least 0.2 millimeter, at least 0.25 millimeter, at least 0.3 millimeter or at least 0.35 millimeter. The protrusions areas may have a height relative to the recess areas of no greater than 2 millimeters, no greater than 1.5 millimeter, no greater than 1 millimeter, no greater than 0.75 millimeter, no greater than 0.5 millimeter, no greater than 0.45 millimeter or no greater than 0.4 millimeter. The height may be of particular protrusion occurrences relative to adjacent areas of recesses. Protrusion occurrences are also referred to herein as anchor protrusions. Such anchor protrusions may be configured to flexibly deform when the conduit is inserted through the fistula for implantation, for example to flexibly deform in a direction opposite the direction of insertion when the anchor protrusions contact tissue disposed in the fistula during insertion. After insertion, the anchor protrusions may over time return to their original shape and extend deeper into adjacent tissue to better anchor the implant device. The mechanical properties of the anchor protrusions may be influenced by materials of construction. Preferred materials of construction for the protrusion areas, and also for the other structured portions of the implant device, are polymeric materials. The polymeric materials may preferably be medical grade materials. Some preferred polymeric materials are silicones and polyurethanes. For enhanced performance, a structural material of construction should have a rigidity that interacts positively with tissue in the vicinity of the fistula, for example to promote load sharing and good anchoring. One preferred material of construction for structural purposes (e.g., for use or a "first material") is a polymeric material (e.g. silicone, polyurethane, silicone-urethane copolymers, silicone-polycarbonate copolymers, polycarbonate-urethane copolymers or silicone-polycarbonate-urethane copolymers) having a durometer (Shore A) in a range having a lower limit of 50, 60, 70 or 80 and an upper limit of 100, 80, 70 or 60, provided that the upper limit must be larger than the lower limit. One preferred range is for a durometer (Shore A) of 60-100, with a range of 70-100 or 80-100 being even more preferred. For some implementations the polymeric material has a durometer (Shore A) of about 60, of about 70, of about 80 or of about 100. Mechanical properties of the protrusion occurrences of the protrusion areas will also be affected by the geometry of the protrusion occurrences. The protrusion occurrences may have a width that tapers, or narrows, in a direction from a base toward a top of the protrusion occurrences, with the base being a portion of a protrusion occurrence disposed toward the internal passage of the conduit and a top of the protrusion occurrence being the extremity of the protrusion occurrence away from the internal passage of the conduit. The width may be transverse to the length of the conduit. The protrusion occurrences may have a width at the base that is no larger than 2 millimeters, no larger than 1.5 millimeters, no larger than 1.25 millimeters, no larger than 1 millimeter or no larger than 0.75 millimeter. One or more of the protrusion occurrences may have a width at the base that is at least 0.2 millimeter, at least 0.3 millimeter, at least 0.5 millimeter, at least 0.75 millimeter or at least 1 millimeter. The protrusion occurrences may have a width adjacent the top that is no larger than 0.75 times width at the base, no larger than 0.5 times the width at the base, or no larger than 0.25 times the width at the base. The protrusion occurrences may have a width midway between the base and the top that is no larger than 0.8 times the width of the base, no larger than 0.7 times the width of the base, no larger than 0.6 times the width of the base or no larger than 0.5 times the width at the base.

The protrusion areas may be provided by a single protrusion occurrence feature located to correspond with the interior of the fistula when the implant device is implanted. In more preferred implementations, the protrusion areas include multiple protrusion occurrences spaced on the exterior of the conduit. The protrusion occurrences may have a center-to-center spacing, in one or more directions, of at least 0.5 millimeter, at least 0.75 millimeter, at least 1 millimeter, at least 1.25 millimeters, at least 1.4 millimeters or at least 1.75 millimeters. The protrusion occurrences may have a center-to-center spacing of no greater than 2.5 millimeters, no greater than 2 millimeters, no greater than 1.75 millimeters or no greater than 1.6 millimeters. The protrusion occurrences may have a center-to-center spacing longitudinally along the conduit. The protrusion occurrences may have a center-to-center spacing that is at least 0.5 times the base width of the protrusion occurrences, or at least 1 times the base width of the protrusion occurrences or at least 2 times the base width of the protrusion occurrences. The protrusion occurrences may have a center-to-center spacing that is no more than 5 times a base width of the protrusion occurrences, no more than 4 times a base width of the protrusion occurrences, no more than 3 times a base width of the protrusion occurrences or no more than 2 times a base width of the protrusion occurrences.

The protrusion areas may be located on a longitudinal portion of the conduit that includes at least a portion of the conduit that will be disposed within a fistula when the implant device is implanted. The protrusion areas may be on a longitudinal portion of the conduit that extends for at least 2 millimeters along the length of the implant device, that extends for at least 3 millimeters along the length of the implant device, that extends for at least 4 millimeters along the length of the implant device, that extends for at least 5 millimeters along the length of the implant device, that extends for at least 6 millimeters along the length of the implant device or that extends for at least 8 millimeters along the length of the implant device. A longitudinal portion of the conduit including the protrusion areas may be no longer than 30 millimeters, no longer than 25 millimeters, no longer than 20 millimeters, no longer than 15 millimeters or no longer than 10 millimeters. A longitudinal portion of the conduit including the protrusion areas may be disposed at least 2 millimeters from the proximal end of the implant device, at least 3 millimeters from the proximal end of the implant device, at least 4 millimeters from the proximal end of the implant device or at least 6 millimeters from the proximal end of the implant device. A longitudinal portion of the conduit including the protrusions may be disposed at least 1 millimeter, at least 2 millimeters, at least 3 millimeters, at least 4 millimeters or at least 6 millimeters from a head of the implant device. Providing significant distance between the head and commencement of the protrusion areas permits the head to better "float" on the surface of tissue, which may enhance patient comfort and device performance. The protrusion areas may be disposed along a longitudinal portion of the conduit with the protrusion areas covering no more than 40% of the area along the longitudinal portion of the conduit, 35% of the area along that longitudinal portion of the conduit, no more than 25% of the area along that longitudinal portion of the conduit or not more than 20% of the area along that longitudinal portion of the conduit. Providing significant spacing between protrusion occurrences may permit better engagement of tissue by the anchoring surface feature. Some or all of the protrusion occurrences may be on the second longitudinal portion of the conduit.

The protrusion areas may comprise at least one circumferential ridge. By circumferential ridge it is meant a ridge that extends around an entire circumference of the conduit. The protrusion areas may comprise at least two, at least three, at least five or at least six circumferential ridges. The protrusion areas may in some implementations comprise not more than 20, not more than 15 or not more than 10 circumferential ridges. The protrusion areas may comprise a spiral ridge. Such a spiral ridge may extend along a longitudinal portion of the conduit. The protrusion areas may comprise a knob or may comprise multiple knobs. The anchoring surface feature may comprise a textured surface, with the protrusion areas comprising protruding portions of the textured surface and the recess areas comprising recess portions of the textured surface.

The length of the implant device may be selected to provide sufficient conduit length for extending through the entire length of the fistula plus any extension distance desired in the lacrimal apparatus proximal to the fistula and in the paranasal sinus distal to the fistula. The length of the implant device and/or of the conduit may be in a range having a lower limit of 2 millimeters, 3 millimeters, 4 millimeters, 5 millimeters, 8 millimeters, 10 millimeters, 12 millimeters or 15 millimeters and an upper limit of 50 millimeters, 40 millimeters, 30 millimeters, 25 millimeters, 20 millimeters, 15 millimeters or 10 millimeters, provided that the upper limit is larger than the lower limit. One preferred range for some implementations when the fistula is between the orbit and the ethmoid sinus or the maxillary sinus is for the length of the implant device and/or for the length of the conduit to be in a range of from 10 millimeters to 30 millimeters, with a range of from 15 millimeters to 25 millimeters being more preferred. By length of the implant device or the conduit it is meant the dimension longitudinally along the implant device or the conduit, as the case may be, from the proximal end to the distal end of the implant device or the conduit, and may be along a longitudinal axis through the internal passage. The length may be a straight line, for example when the internal passage is straight, or the length may be curvilinear or some other shape, for example when the internal passage is not linear. When a reference is made herein to transverse to the length, the reference is to a right angle to the longitudinal direction of the length at that point (e.g., right angle to a line of the length or to a line tangent to a curve of the length). When the conduit includes an extension portion that is extendable and contractible to lengthen and shorten the conduit, the implant device that is fully shortened by full contraction and that is fully lengthened by full extension may be within the noted length ranges.

The implant device may advantageously be designed with a conduit of appropriate width dimensions to fit snuggly within a desired size of fistula. The implant device may have a first exterior width dimension defined by a maximum extent of the protrusion areas transverse to the length of the implant device, with the first exterior width being within a range having a lower limit of 0.75 millimeter, 1 millimeter, 1.25 millimeters, 1.5 millimeters, 1.75 millimeters or 2 millimeters and an upper limit of 8 millimeters, 7 millimeters, 6 millimeters, 5 millimeters, 4 millimeters, 3 millimeters, 2.5 millimeters, 2 millimeters or 1.75 millimeters, provided of course that the upper limit must be larger than the lower limit. The conduit may have a second width dimension defined by the minimum extent of the recess areas transverse to the length of the implant device, and which second exterior width dimension will be smaller than the first exterior width dimension defined by the protrusion areas. The second exterior width dimension defined by the recess areas may be smaller than the first exterior width dimension defined by the protrusion areas by an amount within a range having a lower limit of 0.2 millimeter, 0.25 millimeter, 0.35 millimeter, 0.5 millimeter, 0.6 millimeter or 0.7 millimeter and having an upper limit of 1.5 millimeters, 1 millimeter, 0.9 millimeter or 0.75 millimeter. The height of the protrusion areas may be one-half the difference between the first exterior width and the second exterior width. Either one of or each one of the first exterior width and the second exterior width may be the diameter of a circle.

The implant device may include one or a plurality of side openings through the conduit wall of a distal portion of the conduit, which distal portion may be or include a portion of the conduit that is designed to be disposed within a paranasal sinus when the implant device is implanted to provide fluid access through the implant device to the paranasal sinus. The side openings may be open into the internal passage through the conduit and may provide a passage for fluid communication between the internal passage of the implant device and the paranasal sinus even if the distal opening of the internal passage at the distal end of the conduit were to become blocked or restricted for some reason. One or more of the side openings may be through a wall of the second longitudinal portion of the conduit, and may be though a wall having the second minimum wall thickness. One or more of the side openings may be located within one or more recess areas of an anchoring surface feature of the conduit (e.g., between circumferential ridges). With a thinner minimum wall thickness in the second longitudinal portion of the conduit than the first longitudinal portion of the conduit, the second longitudinal portion of the conduit, and in particular near a distal end of the second longitudinal portion of the conduit, may be more prone to restriction due to collapse of the conduit at or near the distal end, and the side openings provide an alternative fluid access to the paranasal sinus.

The implant device may include a head adjacent to the conduit at the proximal end of the implant device. The implant device may be configured so that when the implant device is implanted to fluidly connect between a location in the lacrimal apparatus in the orbit and a paranasal sinus (e.g., frontal, ethmoid or maxillary sinus), the head is disposed in the lacrimal apparatus in the orbit, such as in the conjunctival cul-de-sac. The head may comprise a flanged tissue engagement surface on a side of the head disposed toward the conduit and configured to engage tissue outside of and adjacent to the fistula when the implant device is implanted. The flanged tissue engagement surface may be a flat surface. The flanged tissue engagement surface may have non-flat surface features configured to improve seating of the surface against tissue, such as for example to inhibit rotation of the implant device within the fistula after implantation. The head may have a face surface opposite the flanged tissue engagement surface and also disposed away from the conduit and disposed away from tissue engaged by the flanged tissue engagement surface when the implant device is implanted. The face surface may be substantially flat. The face surface may be disposed at the proximal end of the implant device and the internal passage may open at the face surface. The separation distance between the face surface and the flanged tissue engagement surface may be in a range having a lower limit of 0.25 millimeter, 0.5 millimeter or 0.75 millimeter and having an upper limit of 2 millimeters, 1.5 millimeters or 1 millimeter. Such separation distance need not be constant across the flanged tissue engagement surface and face surface. A maximum separation distance between the face surface and the flanged tissue engagement surface may be referred to as the depth of the head, and such depth may be in a range described above for the separation distance between the face surface and the flanged tissue engagement surface. The flanged tissue engagement surface need not be continuous and may be divided into multiple distinct surface portions. For example, the flanged tissue engagement surface may include a first flanged portion disposed to one side of the internal passage and a second flanged surface portion disposed to a second side of the internal passage that is opposite the first side. Each of the face surface and the flanged tissue engagement surface may have a length dimension that represents a maximum separation distance between points on an outer edge of the respective surface, and may each have a width dimension that is a maximum separation distance between points on the outer edge transverse to the length dimension. The length dimensions of the face surface and the flanged tissue engagement surface may be the same or may be different. The width dimensions of the face surface and the flanged tissue engagement surface may be the same or may be different. The face surface and the flanged tissue engagement surface may have corresponding outer edges. The length dimension of any or all of the face surface, the flanged tissue engagement surface and the head may be larger than a first exterior width of the conduit defined by an extent of the protrusion areas transverse to the length of the implant device, when the implant device includes an anchoring surface feature such as summarized above. The length dimension of any or all of the face surface, the tissue engagement surface and the head may be in a range having a lower limit of 1 millimeter, 2 millimeters, 2.5 millimeters, 2.75 millimeters, 3 millimeters, 3.5 millimeters, 4 millimeters or 5 millimeters and an upper limit of 10 millimeters, 8 millimeters or 7 millimeters. The width dimension of any or all of the face surface, tissue engagement surface and the head may be in a range having a lower limit of 0.5 millimeter, 1 millimeter, 1.5 millimeters, 1.75 millimeters or 2 millimeters and an upper limit of 5 millimeters, 4 millimeters, 3 millimeters, 2.5 millimeters or 2 millimeters, provided as always that the upper limit is larger than the lower limit. The length dimension of any or all of the face surface, the flanged tissue engagement surface and the head may be at least 0.5 millimeters, at least 0.75 millimeter, at least 1 millimeter, at least 2 millimeters, at least 3 millimeters or at least 4 millimeters larger than such first exterior width of the conduit defined by an extent of the protrusion areas, when the implant device includes an anchoring surface feature such as summarized above. A ratio of the length of any of or all the face surface, the flanged tissue engagement surface and the head to such a first exterior width of the conduit may be at least 1.5 or at least 2. Such a ratio may be smaller than 4, smaller than 3 or smaller than 2.5. The width of any or all of the face surface, the flanged tissue engagement surface and the head may be not larger than, or may be smaller than (e.g., by at least 0.1 mm or by at least 0.2 mm), such a first exterior width of the conduit defined by an extent of the protrusion areas, when the implant device includes an anchoring surface feature such as summarized above. A ratio of the length dimension to the width dimension for any or all of the face surface, the flanged tissue engagement surface and the head may be in a range having a lower limit of 1, 1.25, 1.5, 2 or 2.5 and an upper limit of 5, 4, 3 or 2.5, provided of course that the upper limit must be larger than the lower limit. Having a larger length dimension to width dimension on the head is particularly preferred when the head will be located in the orbit between an eyeball and a medial corner of the palpebral fissure (e.g., between the lacrimal caruncle and the plica semilunaris or through the lacrimal apparatus), because the length dimension may advantageously align in a vertical direction next to the eyeball and will help provide sufficient flanged surface area to effectively anchor the implant device on the proximal end and impede conjunctival tissue from covering the opening into the internal passage of the implant device, compensating for the narrower width. This is particularly advantageous when using polymeric materials of construction as described above.

The lacrimal apparatus and a paranasal sinus may be in fluid communication through the internal passage of the implant device when the implant device is implanted. The conduit may extend from adjacent the proximal end of the implant device. The conduit may extend to adjacent the distal end of the implant device. The internal passage may have a first end open at the proximal end and a second end open at the distal end, and when the implant device is implanted the first end of the internal passage may open in the lacrimal apparatus and the second end of the internal passage may open in the paranasal sinus.

The implant device may be configured for implantation with the conduit passing through a fistula between a location in a lacrimal apparatus within the orbit and a paranasal sinus selected from the group consisting of a frontal sinus, an ethmoid sinus, a maxillary sinus and a sphenoid sinus, with a frontal sinus, a maxillary sinus or an ethmoid sinus being preferred, with an ethmoid sinus or a maxillary sinus being more preferred, and with an ethmoid sinus being particularly preferred. The implant device may be configured for the conduit to pass through a first paranasal sinus and into a second paranasal sinus in which the distal end of the implant device is disposed when implanted. The implant device may provide fluid communication between the lacrimal apparatus and the second paranasal sinus and may or may not also provide fluid communication between the lacrimal apparatus and the second paranasal sinus. For example, the portion of the conduit passing through the first paranasal sinus may have an impermeable wall to prevent fluid communication with the first paranasal sinus or may have one or more openings through the wall that provide permeability through the wall and a fluid path for fluid communication to the first paranasal sinus, in which case fluids (e.g., treatment formulations) may be introduced into either one or both of the first and second paranasal sinuses. As one example, an implant device may be configured to be implanted with a proximal end in the lacrimal apparatus in the orbit and a distal end in an ethmoid sinus with the conduit passing through a frontal sinus or a maxillary sinus.

Various feature refinements and additional features are applicable to other methods.

A method may be or involve administering a treatment composition to a paranasal sinus through an implant device of the first aspect that fluidly connects the lacrimal apparatus with the paranasal sinus.

Various feature refinements and additional features are applicable to the packaged product aspect and the method aspect involving implanting an implant device of such a packaged product.

The implant device of the product may include any feature or combination of features disclosed in relation to the first aspect or any other aspect. The implant device may be according to the first aspect, or may not be according to the first aspect. The implant device may be according to the first aspect including feature (xvi).

The storage liquid may provide for enhanced wettability of some or all exterior surfaces of the implant device (e.g., surfaces other than the surfaces of the walls of an internal passage within the implant device). In some implementations, all exterior surfaces of the implant device may be in contact with the storage liquid. Internal passage surfaces may also be in contact with the storage liquid. Substantially all surfaces of the implant device may be in contact with the storage liquid. The implant device may be immersed in a reservoir of the storage liquid.

The storage liquid may comprise an aqueous liquid, which may be a buffer solution. The storage liquid may include a wetting agent, which may improve hydration of at least a portion of exposed surfaces of the implant device following implantation. In some implementations, the implant device includes a head disposed in the lacrimal apparatus when the implant device is implanted, and the wetting agent may improve hydration of exterior surfaces of the head within the lacrimal apparatus. In some implementations, the implant device may include a distal portion disposed in the paranasal sinus when the implant device is implanted, and the wetting agent may improve hydration of exterior surface of such distal portion following implantation. A wetting agent may include any material that provides enhanced wettability of any such exterior surfaces (e.g., of a head or a distal portion of the implant device) to wetting by biological fluid, for example wetting of head surfaces by lacrimal fluid. The wetting agent may be any wetting agent, for example as discussed above. On preferred wetting agent is hyaluronic acid.

The sterile packaging may include any sterile barrier enclosure, for example in the form of a sealed bag, pouch or tray. A packaged product may include a plurality of such implant devices, with the sterile packaging including a plurality of sealed compartments each having disposed therein an implant device in contact with storage liquid. The sterile packaging may include a multi-compartment tray comprising such an implant device sealed within each of a plurality of such compartments of the tray. Each such compartment may be sealed so that each such sealed compartment is individually unsealable to remove an implant device from a compartment without unsealing other compartments. In some implementations, the sterile packaging may include a multi-compartment tray (e.g., of a plastic material) with compartments sealed with a foil lid.

During a method for implanting an implant device from a packaged product, the implant device may have at least a residual portion of the storage liquid, which may include at least a portion of a wetting agent, covering at least a portion of the implant device.

These and other aspects of the disclosure, and possible feature refinements and additional features therefore, will be further understood with reference to the drawings, to the description provided below and to the claims.

BRIEF DESCRIPTION OF THE DRAWINGS

The drawings are included to aid in the understanding of various aspects of the disclosure and possible feature refinements and additional features applicable thereto. Features shown in the drawings are presented for purposes of illustration only, and are not necessarily to scale and are not necessarily detailed in every respect.

DETAILED DESCRIPTION

Figure 1:
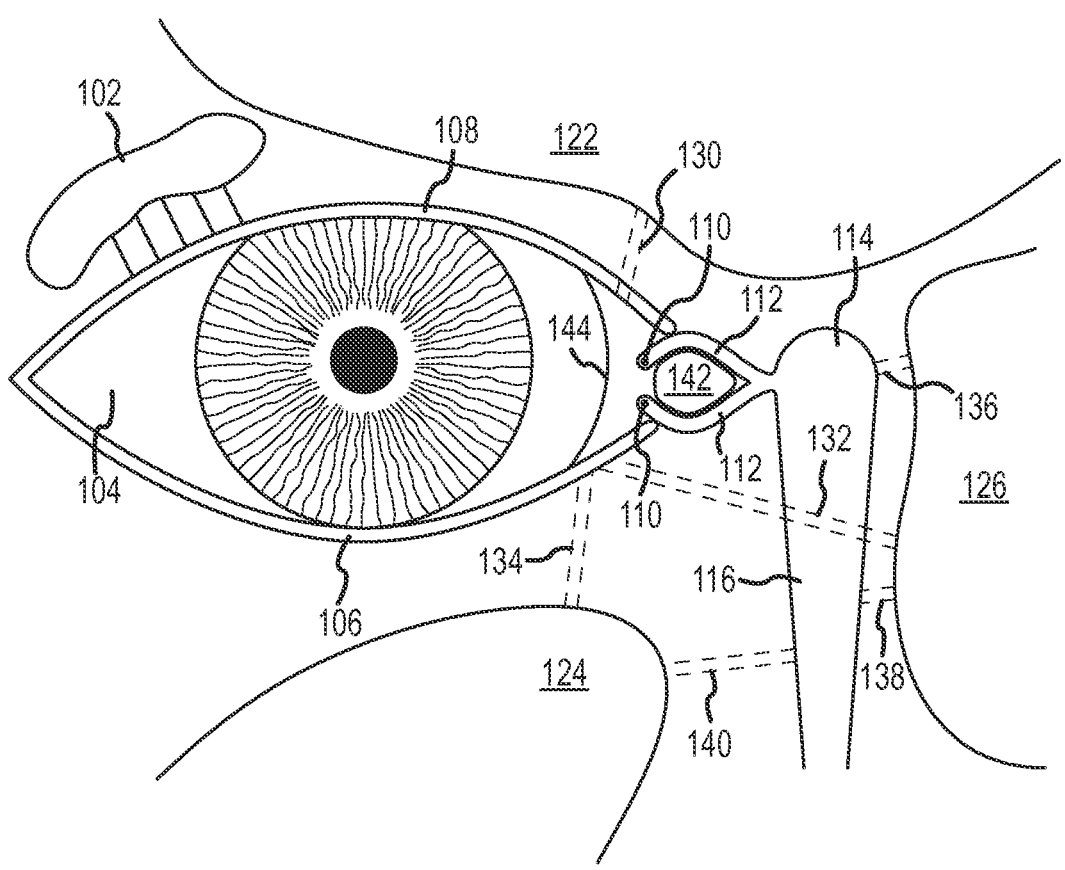
FIG. 1 is an illustration showing some example routes for an implant to provide fluid access from the lacrimal apparatus to a paranasal sinus.

The terms "lacrimal apparatus" and "lacrimal system" are used interchangeably herein to refer to the collection of physiological components that accomplish the production and secretion of lacrimal fluid to lubricate the eyeball, containment of lacrimal fluid in a reservoir of lacrimal fluid in the orbit and drainage of lacrimal fluid from the orbit to the nasal cavity. The lacrimal apparatus includes the lacrimal glands, the tear drainage system and the reservoir of lacrimal fluid located between the lacrimal glands and the tear drainage system. The reservoir of lacrimal fluid includes the eyelid margins and the conjunctival sac (and including the pool of tears in the lower conjunctival cul-de-sac that is sometimes referred to as the lacrimal lake). The tear drainage system includes the puncta, canaliculi and nasolacrimal duct (including the so-called lacrimal sac located at the top of the nasolacrimal duct) through which excess tears drain to Hasner's valve and into the nasal cavity. FIG. 1 shows generally the lacrimal apparatus. Lacrimal fluid is produced and secreted from lacrimal glands 102 to lubricate the surface of the eyeball 104 disposed within the orbit. Lacrimal fluid forms a coating over the eyeball 104 and is generally contained within the conjunctival sac (the space between the lower eyelid 106, upper eyelid 108 and eyeball 104 that is lined by the conjunctiva). Excess lacrimal fluid is conducted to the vicinity of the medial canthus (medial corner of the eye) and drains through the lacrimal puncta 110 into the lacrimal canaliculi 112 and into the lacrimal sac 114 of the nasolacrimal duct 116. The lacrimal fluid then drains from the nasolacrimal duct 116 through Hasner's valve and into the nasal cavity.

As used herein, a fistula between the lacrimal apparatus and a paranasal sinus refers to an artificially-created passage that fluidly connects the lacrimal apparatus with a paranasal sinus. Such a fistula may be surgically created. The paranasal sinuses include the frontal sinuses, maxillary sinuses, ethmoid sinuses and sphenoid sinuses, which are cavities contained within frontal, maxilla, ethmoid and sphenoid bones, respectively. The paranasal sinuses drain into the nasal cavity. FIG. 1 also shows the general proximity of the frontal sinus 122, maxillary sinus 124 and ethmoid sinus 126 relative to features of the lacrimal apparatus and some example fistula routes shown by dashed lines. A first example fistula route 130 is from the orbit to the frontal sinus. A second example fistula route 132 is from the orbit to the ethmoid sinus 126. A third example fistula route 134 is from the orbit to the maxillary sinus 124. A fourth example fistula route 136 is from the lacrimal sac 114 at the top of the nasolacrimal duct 116 to the ethmoid sinus 126. A fifth example fistula route 138 is from the nasolacrimal duct 116 at a location below the lacrimal sac 114 to the ethmoid sinus 126. A sixth example fistula route 140 is from the nasolacrimal duct 116 at a location below the lacrimal sac 114 to the maxillary sinus 124. The example fistula routes shown in FIG. 1 are for purposes of general illustration only and not to show precise locations where a fistula might be formed to connect a part of the lacrimal apparatus with the corresponding paranasal sinus. Although not shown in FIG. 1, example fistula routes to the sphenoid sinus include from the orbit to the sphenoid sinus and from the nasolacrimal duct 116 to the sphenoid sinus.

Figure 2:
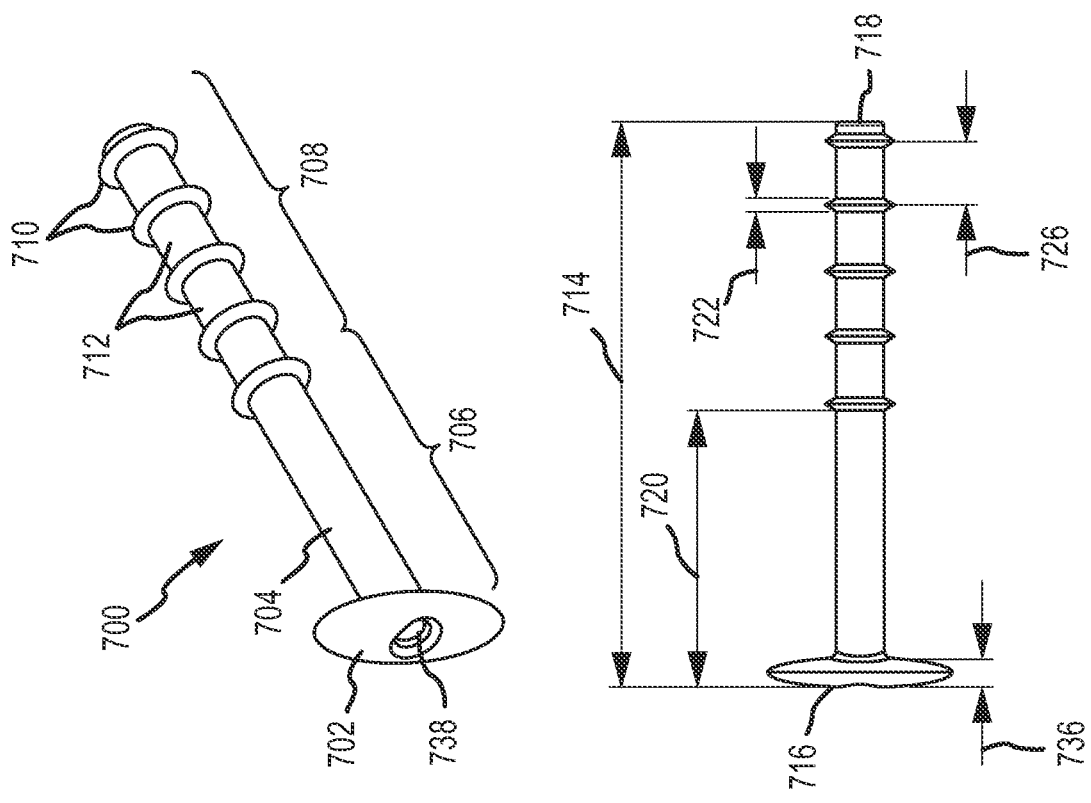
FIG. 2 shows perspective, top, side and end views of an embodiment of an implant device.
Figure 2:
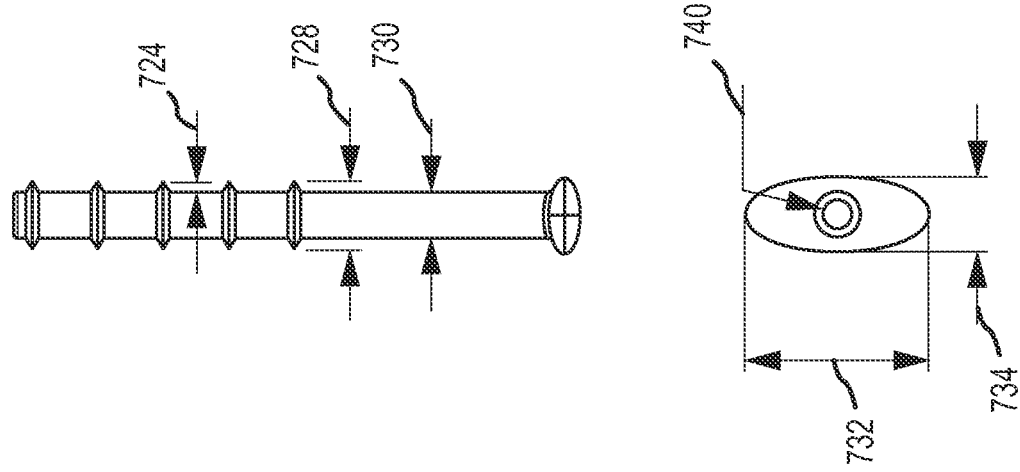
Figure 3:
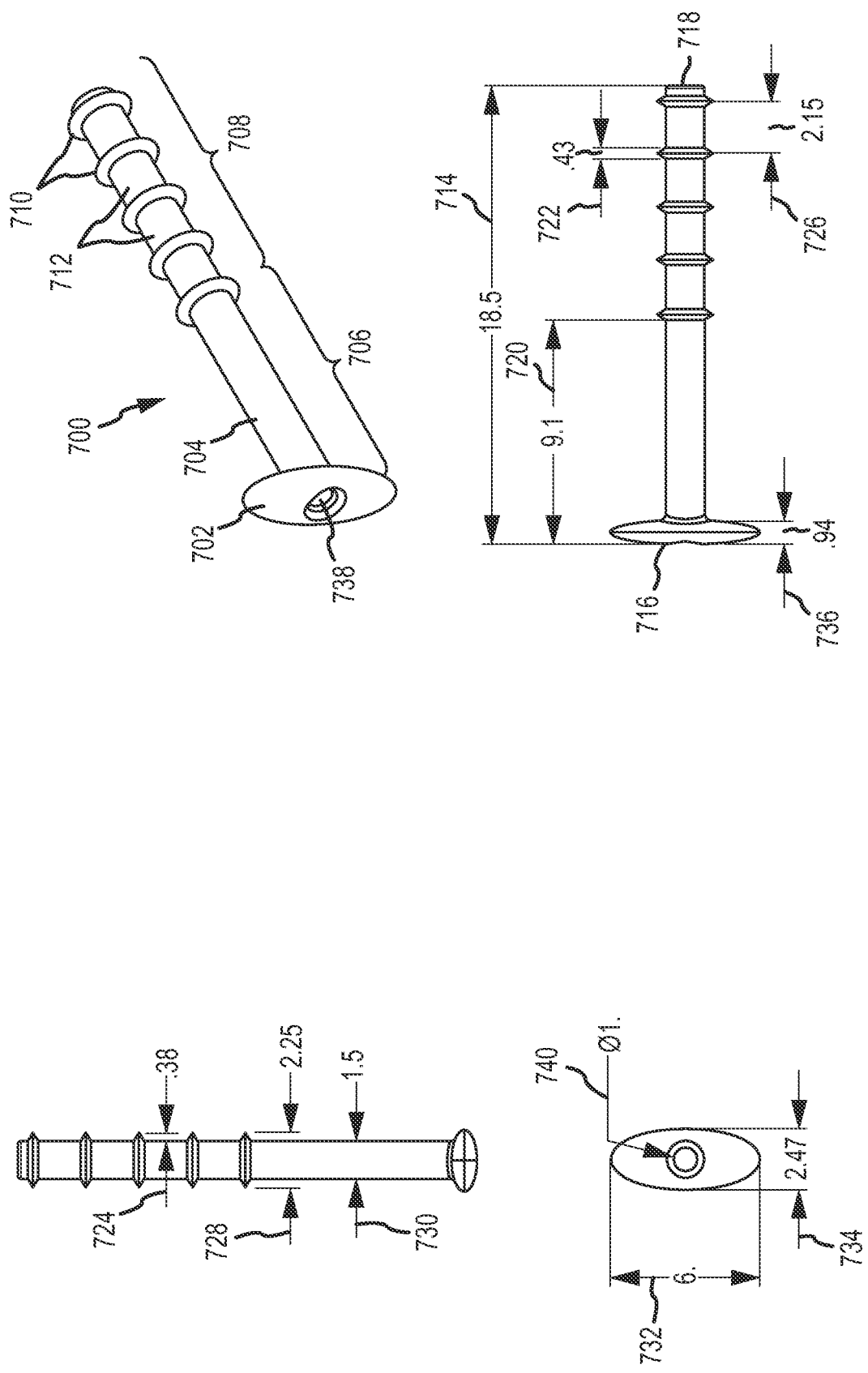
FIG. 3 shows perspective, top, side and end view of an embodiment of an implant device showing some possible example dimensions.

FIG. 2 shows an implant device 700 with a head 702 and a conduit 704. The conduit 704 includes a first longitudinal portion 706 and a second longitudinal portion 708 disposed distal of the first longitudinal portion 706. The first longitudinal portion 706 includes a smooth exterior surface and the second longitudinal portion 708 includes an anchoring surface feature including anchor protrusions 710, in the form of spaced circumferential ridges, and recess areas 712 between the anchor protrusions 710. The length of the first longitudinal portion 706, located before the beginning of the anchoring surface feature of the second longitudinal portion 708, may advantageously be disposed in conjunctival tissue adjacent the head 702 when implanted to "float" for patient comfort and to facilitate performance of post-implantation medical procedures without disruption of implant anchor stability. The anchoring features of the second longitudinal portion 708 may advantageously be located a distance from the head 702 so that one or more of the anchor protrusions 710 are located in the vicinity of the paranasal sinus bone wall that is penetrated by the implant device 700 when implanted, preferably with one or more of the anchor protrusions disposed on each side of the bone. In the embodiment shown in FIG. 2, the exterior width of the conduit 704 is substantially the same for the whole length of the first longitudinal portion 706 and in the recess areas 712 of the second longitudinal portion 708. The conduit 704 has a circular cross-section, so that the exterior width of the conduit 704 at any location along the conduit 704 is represented by the diameter of the circular cross-section of the conduit 704 at that location. As shown in FIG. 2, the implant device 700 has a length 714 from a proximal end 716 to a distal end 718 of the implant device 700. The beginning of the second longitudinal portion 708 is located a distance 720 distal from the proximal end 716. The anchor protrusions 710 have a width 722 at the base of the anchor protrusions 722 and a height 724 above the adjacent recess areas 712. The anchor protrusions 710 are spaced on a center-to-center spacing 726. The conduit 704 has a maximum exterior width 728 corresponding with the tops of the anchor protrusions 710, equal to the diameter of the circle of the cross-section through the conduit 704 at the top of the anchor protrusions 710. The conduit 704 has a minimum exterior width 730 along the length of the first longitudinal portion 706 and in the recess areas 712 of the second longitudinal portion 708 of the conduit 704, and which is equal to the diameter of the circular cross-section at those locations. The head 702 has a length dimension 732, a width dimension 734 and a depth dimension 736. The implant device 700 has an internal passage 738 extending between the proximal end 716 and the distal end 718 and through the length of the conduit 704. The internal passage 738 has a width 740, which in this embodiment is equal to a diameter of the circular cross-section of the internal passage 738. FIG. 3 shows the same implant device 700 as shown in FIG. 2 with some exemplary dimensions, in millimeters, for one nonlimiting example for a configuration for the implant device 702.

Figure 4:
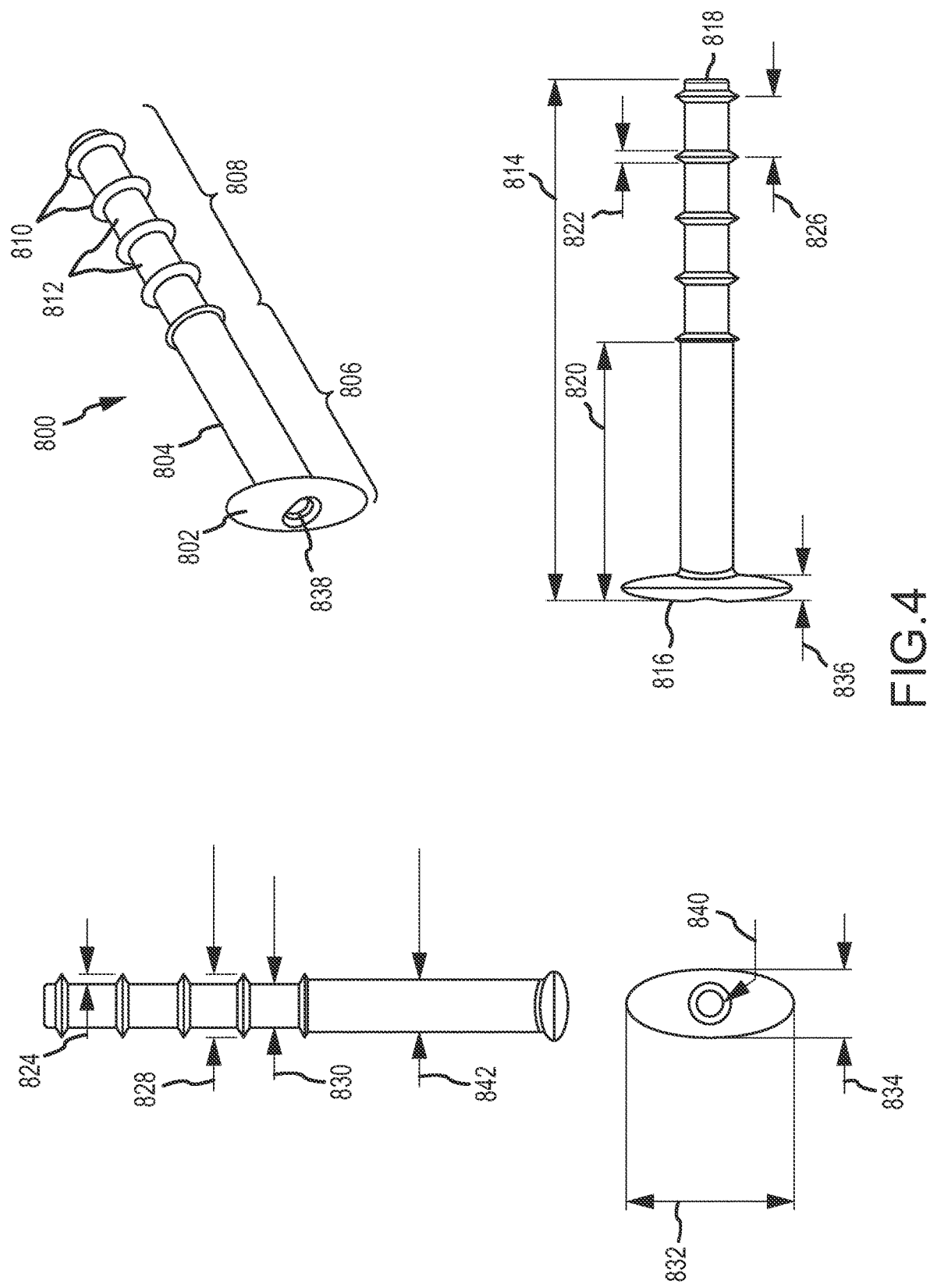
FIG. 4 shows perspective, top, side and end views of an embodiment of an implant device.

FIG. 4 shows an implant device 800 that is similar to the implant device 700 shown in FIGS. 2 and 3, except including a first longitudinal portion of a conduit having a thicker wall than recess areas of the anchoring surface feature of a second longitudinal portion of the conduit. The thicker wall in the first longitudinal portion of the conduit provides added rigidity to that portion of the conduit to facilitate pushing the implant device 800 into place during an implantation procedure, while the thinner wall in the recess areas of the second longitudinal portion of the conduit permit that portion to more easily deform and fit through a fistula during implantation and then to expand to engage tissue and anchor the implant device 800. More specifically as shown in FIG. 4, the implant device 800 includes a head 802 and a conduit 804. The conduit 804 has a first longitudinal portion 806 and a second longitudinal portion 808 located distal of the first longitudinal portion 806. The first longitudinal portion 806 includes a substantially smooth exterior surface with a substantially constant exterior width, which is the diameter of the circular cross-section of the conduit 804 along the first longitudinal portion 806. The second longitudinal portion 808 includes an anchoring surface feature including anchor protrusions 810, in the form of circumferential ridges, and recess areas 812 in the spaces between the anchor protrusions 810. Various dimensions of the implant device 802 are illustrated in FIG. 4, similar to the illustration provided for the implant device 700 in FIG. 2. The implant device 800 has a length 814 from a proximal end 816 to a distal end 818 of the implant device 800. The beginning of the second longitudinal portion 808 is located a distance 820 distal of the proximal end 816. The anchor protrusions have a width 822 at the base and a height 824 above the adjacent recess areas 812. The anchor protrusions are spaced on a center-to-center spacing 826. The conduit 804, and also the second longitudinal portion 808, has a maximum exterior width 828 occurring at the tops of the anchor protrusions 810, and equal to the diameter of the circular cross-section of the conduit 804 through the tops of the anchor protrusions 810. The conduit 804, and the second longitudinal portion 808, of the conduit 804 have a minimum exterior width 830 located at the recess areas 812. The head 802 has a length dimension 832, a width dimension 834 and a depth dimension 836. The implant device 800 has an internal passage 838 extending between the proximal end 816 and the distal end 818 and through the length of the conduit 804. The internal passage 838 has a width 840, which in the embodiment shown in FIG. 4 is equal to a diameter of the circular cross-section of the internal passage 838.

Figure 5:
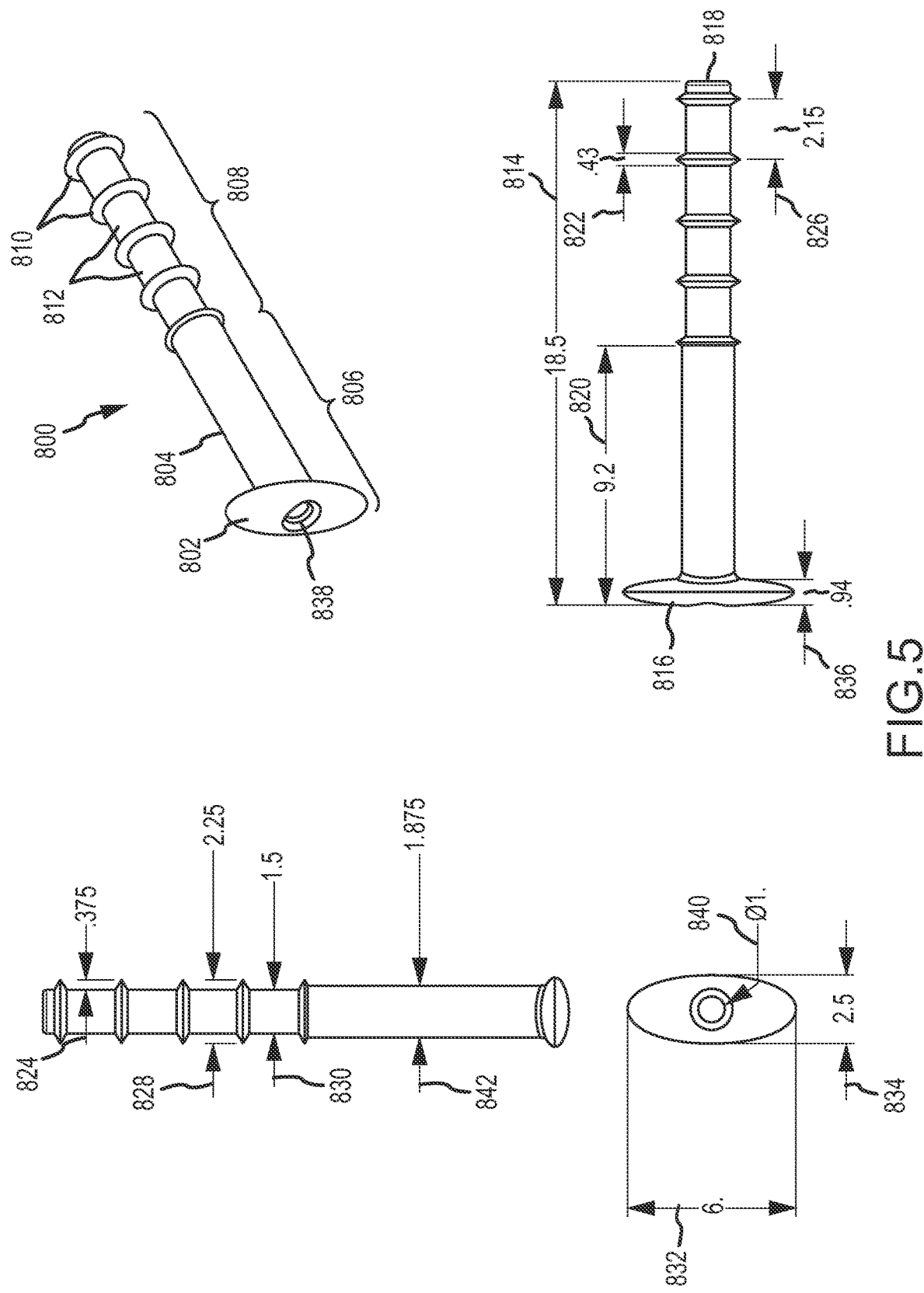
FIG. 5 shows perspective, top, side and end view of an embodiment of an implant device showing some possible example dimensions.

With continued reference to FIG. 4, the wall thickness of the conduit 804, (thickness of the wall between the internal passage 838 and the exterior surface of the conduit 804) is greater along the first longitudinal portion 806 than in the recess areas 812 of the second longitudinal portion 808. The internal passage 838 has a constant width along the length of the conduit 804, such that the greater wall thickness of the conduit 804 along the first longitudinal portion 806 results in an exterior width 842 that is larger than the minimum exterior width 830 in the recess areas 812. The maximum exterior width 828 at the anchor protrusions 810 is larger than the exterior width 842 along the first longitudinal portion 806. FIG. 5 shows some exemplary dimensions, in millimeters, for one nonlimiting example for a configuration of the implant device 800.

Figure 6:
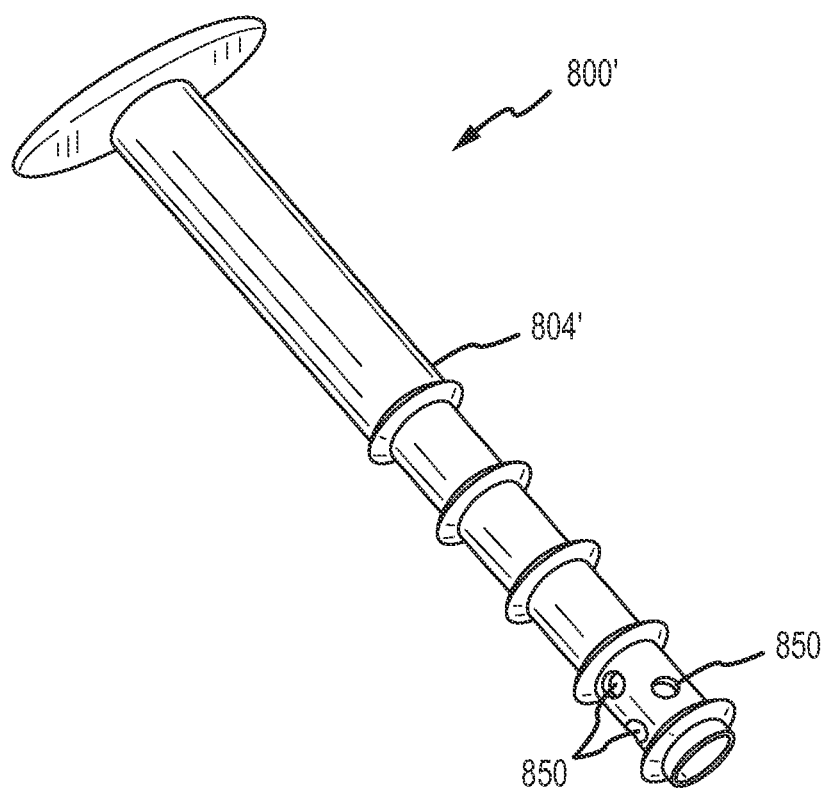
FIG. 6 is a perspective view of an embodiment of an implant device.

FIG. 6 shows a variation on the implant device 800 of FIG. 4. The implant device 800' variation of FIG. 6 has the same features as the implant device 800 of FIG. 4, except that the implant device 800' includes a plurality of side openings 850 (which may also be referred to as holes, apertures or ports) through the wall of a distal portion of the conduit 804'. The side openings 850 may be located on a portion of the conduit wall that would be disposed in the paranasal sinus when the implant device 800' is implanted, such that the side openings 850 may provide a passage for fluid communication between the internal passage of the implant device 800' and the paranasal sinus even if the distal opening of the internal passage at the distal end of the conduit 804' were to become blocked or restricted for some reason. In the particular implementation shown in FIG. 6 for the implant device 800', the side openings 850 are located in a recess area between a pair of circumferential ridges of an anchoring surface feature of the conduit 804'. FIG. 6 shows the side openings 850 located in only one recess area between one pair of circumferential ridges, but one or more similar side openings could also or alternatively be located in a more proximal recess area between a different pair of the circumferential ridges.

Figure 7:
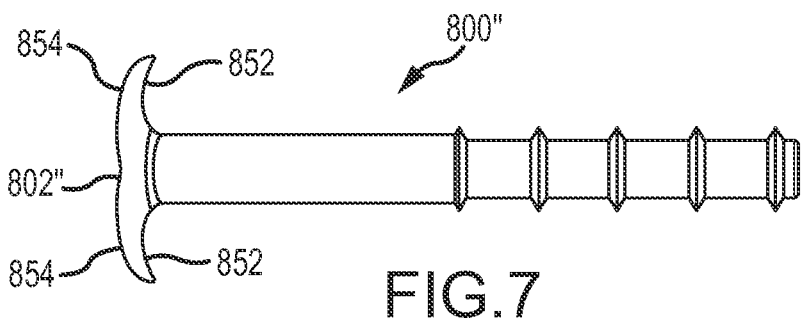
FIG. 7 is a side view of an embodiment of an implant device.

FIG. 7 shows another example variation on the implant device 800 of FIG. 4. The implant device 800" variation shown in FIG. 7 has the same general features as the implant device 800 of FIG. 4, but with a different head design. The head 802" shown in FIG. 7 has flanged portions with a distal side having concave surfaces 852 disposed towards the distal end of the implant device 800". The flanged portions of the head 802" have a proximal side with convex surfaces 854 disposed away from the distal end of the implant device 800". The concave surfaces 852 may provide an advantage of better conforming with soft tissue within the orbit engaged by the distal side of the flanged head portions when the implant device 800" is implanted to fluidly connect the lacrimal apparatus in the orbit with a paranasal sinus. The convex surfaces 854 also may better conform with the surface of such soft tissue when the implant device 800" is implanted. The head 802" may thus help reduce possibility for a foreign body sensation when the implant device 800" is implanted.

Figure 8:
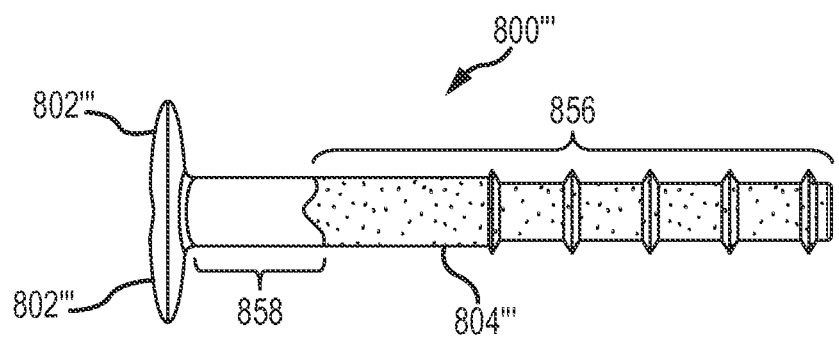
FIG. 8 is a side view of an embodiment of an implant device.

FIG. 8 shows another example variation on the implant device 800 of FIG. 4. The implant device 800''' variation shown in FIG. 8 has the same general features as the implant device 800 of FIG. 4, but includes a conduit 804''' including a radiopaque portion 856 extending over a significant length of the conduit 804'''. The conduit 804''' also includes a radiotransparent portion 858 located adjacent the proximal end of the conduit 804'''. The head 802''' is also radiotransparent. The head 802''' in particular is preferably clear and substantially transparent or translucent to visible light so that when the implant device 800''' is implanted with the head 802''' disposed in the orbit, the head 802''' is not highly visible. In contrast, the radiopaque portion 856 of the conduit 804''' may be easily imaged by radiation, for example by x-ray imaging, to verify the positioning of the conduit 804''' in a patient's body when the implant device 800''' is implanted or at any time post implantation, for example to verify proper implant placement. As an alternative to the variation shown in FIG. 8, such an implant device could be made to be entirely radiopaque, however such a variation may be not preferred for some applications due to enhanced visibility of the head 802''', which may be generally less aesthetically pleasing to patients in which the implant device is implanted. The implant device 800''' may be made, for example, by introducing a radiotransparent resin composition into a proximal end of a mold and a radiopaque resin composition into a distal end of the mold, with an interface between the different resin compositions forming at an intermediate location in the mold based on the relative proportions of the different resin compositions introduced into the mold. For example, such a radiopaque portion may be a resin composition including a radiopaque agent (e.g., particulate radiopaque filler), while the radiotransparent composition may include the same or a different resin (e.g., silicone or polyurethane resin).

Figure 9:
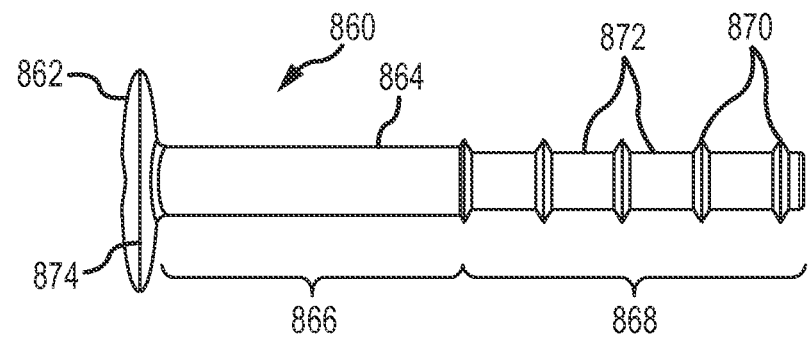
FIG. 9 is a side view of an embodiment of a preliminary implant device form.

Reference is now made to FIGS. 9-15 in relation to various examples of methods of making a paranasal sinus implant device in which a preliminary form is modified to make a modified implant device form, which modified implant device form may be a final implant device product or may be a new preliminary form to be further processed in the manufacture of a further intermediate form or a final product. FIG. 9 shows a preliminary form 860 including a preliminary head structure 862 and a preliminary conduit structure 864. The preliminary conduit structure 864 includes a first longitudinal portion 866 and a second longitudinal portion 868. First longitudinal portion 866 has a substantially smooth exterior surface with a substantially constant exterior width of circular cross-section. The second longitudinal portion 868 includes an anchoring surface feature including anchor protrusions 870, in the form of circumferential ridges, and recess areas 872 in the spaces between the anchor protrusions 870. The first longitudinal portion 866 of the preliminary conduit 864 may have a larger minimum wall thickness than the second longitudinal portion 808. The preliminary conduit 864 is illustrated with features substantially as described with respect to the conduit of the implant device shown in FIG. 4, but could be of a different design, for example with one or more features shown in any of FIG. 2-3, 6-8 or 16-26. The preliminary head structure 862 is also illustrated with features substantially as shown in FIG. 4, but could be of a different design, for example with one or more features shown in any of FIG.

2-3, 6-8 or 16-26. As shown in FIG. 9, the preliminary head structure 862 includes flash 874 around the perimeter of the preliminary head 862. For example, the preliminary implant device form 860 may be an initial mold product (e.g., from injection molding, compression molding or transfer molding) of one or more resin compositions (e.g., silicone or polyurethane resin), and the flash 874 may be formed at a joint between parts of the mold. Presence of such flash 874 may contribute to a patient experiencing a foreign body sensation when implanted. Such flash 874 may be removed to smooth the surface of the head and reduce potential for such a foreign body sensation and may also help to reduce potential for biofilm formation on the smoother surface. Such removal of the flash 874 may be effected by any removed technique, for example by trimming, cryogenic tumbling or laser ablation.

Figure 10:
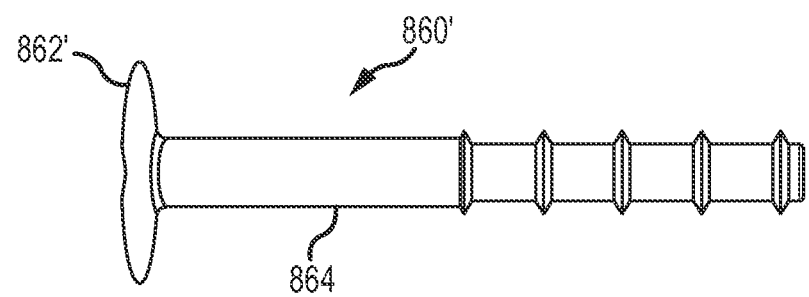
FIG. 10 is a side view of an embodiment of a modified implant device form prepared by modification of the preliminary implant device form of FIG. 9.

FIG. 10 shows a modified implant device form 860' with a modified head structure 862' after removal of the flash 874 from the preliminary implant device form 860 of FIG. 9. The preliminary conduit 864 is unaltered in FIG. 10. The modified implant device 860' may be used as a final implant device product, or may be used as a further preliminary form that is further modified. For example, following removal of the flash 874, the modified head structure 862' may be further modified by forming a thin layer of softer material over the modified head structure 862', for example a layer of a silicone material that is softer than the initial structural material of the preliminary head structure 862. Such a layer of softer material may be formed, for example, by dip molding or spray molding a softer layer of material on top of the modified head structure 862'.

Figure 11:
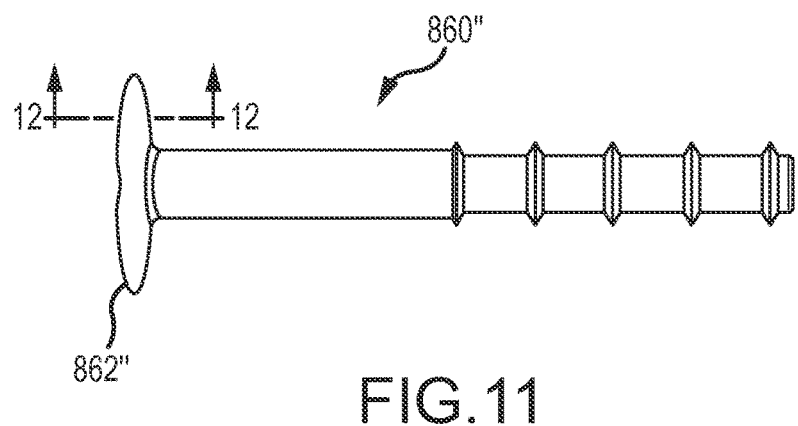
FIG. 11 is a side view of a further modified implant device form prepared by modification of the modified implant device form of FIG. 10.

FIG. 11 shows an example following formation of such a softer material layer, with the implant device form now designated as a further modified form 860". The modified implant device form 860" includes a modified head structure 862" that is slightly enlarged by addition of such a thin layer of softer material. As shown in the sectional view of FIG. 12, the modified head structure 862" includes a layer of softer material 876 formed over original structural material 878 of the original head form 862 of FIG. 9. The presence of the softer material 876 may further enhance compatibility with soft tissue within the orbit when implanted, which may further help to avoid a foreign body sensation following implantation. Moreover, such a carefully applied layer of softer material 876, such as may be formed by dip coating, may have a significantly smoother exterior surface than the exterior surface of the original preliminary head structure 862 of FIG. 9 or the modified head structure 862' of FIG. 10. Such smoother exterior surface may further assist in reducing potential for a foreign body sensation following implantation and may also reduce potential for biofilm formation on exposed surfaces of the modified head structure 862". The modified implant device form 860" may be used as a final implant device product, or may be used as a further preliminary form that is further modified.

Figure 12:
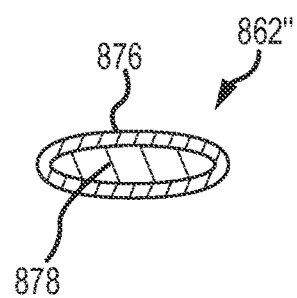
FIG. 12 is a sectional view of a portion of the head of the modified implant device form of FIG. 11.
Figure 13:
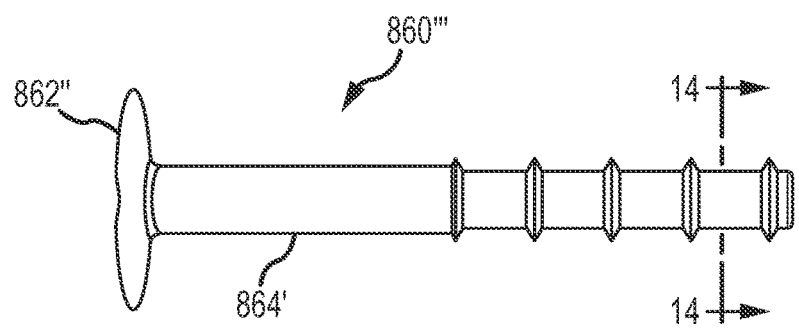
FIG. 13 is a side view of a further modified implant device form prepared by modification of the modified implant device form of FIG. 11.
Figure 14:
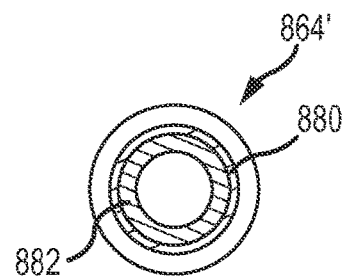
FIG. 14 is a sectional view through a portion of the conduit of the modified implant device form of FIG. 13.

In a similar manner to the formation of the layer of softer material 876 shown in FIGS. 11 and 12, the conduit may be similarly modified by forming a thin layer of softer material over a portion of the preliminary conduit structure 864. FIG. 13 shows a further modified implant device form 860'" including a modified conduit structure 864' including such a layer of softer material formed over a distal portion of the initial preliminary conduit structure 864 shown in FIG. 9. As shown in the sectional view of FIG. 14, the modified distal portion of the modified conduit structure 864' includes a layer of softer material 880 over the original structural material 882 of the initial preliminary conduit structure 864. Such a layer 880 could, for example, be of a silicone material that is softer than the initial structural material of the preliminary conduit structure 864. Such a layer of softer material 880 may advantageously be provided only on a distal portion of the conduit that extends into the paranasal sinus when the implant device is implanted, although such a softer layer could be placed over other portions of the conduit as well if desired. In some preferred implementations, the harder structural material 882 would remain exposed along the portion of the conduit that passes through the wall of the paranasal bone (e.g., the ethmoid bone) and that engages soft tissue immediately proximal of such bone. The harder structural material 882 provides better mechanical interaction for anchoring an implant device. However, the softer material and smoother surface of the layer 880 may provide a reduced susceptibility to formation of biofilms thereon relative to the unmodified distal portion of the initial preliminary conduit structure 864. The modified implant device form 860'" may be used as a final implant device product or may be used as a further preliminary form that is further modified.

Figure 15:
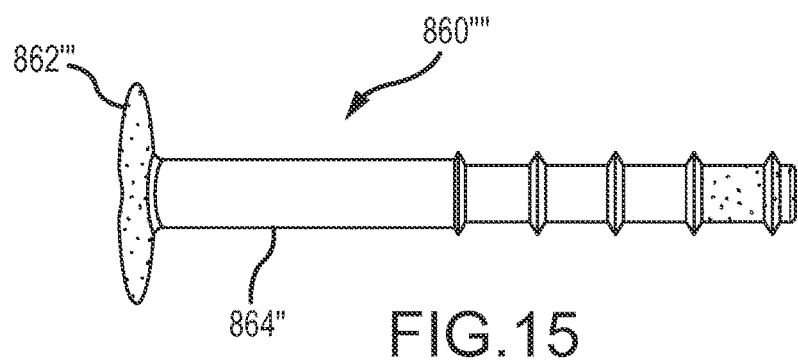
FIG. 15 is a further modified implant device form prepared by modification of the modified implant device form of FIG. 13.

Such a modified head form 862" or modified conduit form 864' may be further modified, for example, by applying one or more additive materials to one or both of the softer material layers 876 and 880. Such additive materials may include, for example, a wetting agent, an antimicrobial agent and/or other additive materials. FIG. 15 shows the conduit form 860'" of FIG. 13 after further modification to apply an additive material to each of the layers of softer material 876 and 880. FIG. 15 shows the further modified implant device form 860"" with shading on a further modified head structure 862'" and a further modified conduit structure 864" to show addition of such an additive material to the layer of softer material 876 and the layer of softer material 880. Depositing a wetting agent (e.g., polyvinylpyrrolidone, polyethylene glycol or hyaluronic acid) may further help to prevent biofilm formation on the modified head form 862'" and the distal portion of the modified conduit form 864". Such a wetting agent may be deposited from a solution, for example, by dipping or spraying, followed by drying and optionally heating to cure the composition or to improve adhesion of the wetting agent. Addition of an antimicrobial agent may further assist to reduce potential formation of biofilms on the modified head form 862'" and the distal portion of the modified conduit form 864". For example, a silver salt may be deposited from the solution applied by dripping or spraying, followed by drying and optionally heating. As another example, silver metal may be deposited by physical vapor deposition or chemical vapor deposition. As another example, an antimicrobial peptide may be deposited from a solution or slurry or may be covalently bonded to exposed polymer (e.g., silicone) of one or both of the softer material layers 876 and 880. As a further example, a polymeric antimicrobial agent (e.g., polyethylene oxide or polyethylene glycol) may be deposited by dip or spray coating from a solution contrary they polymeric antimicrobial agent. In some preferred implementations a wetting agent (e.g., PVP, PEG, hyaluronic acid) and antimicrobial agent (e.g., a polymeric antimicrobial agent and/or an antimicrobial peptide) may be applied together to the same surface.

Figure 16:
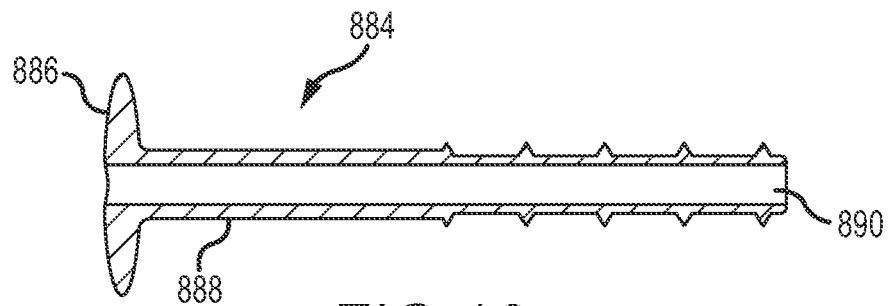
FIG. 16 is sectional view of an embodiment of a preliminary implant device form.
Figure 17:
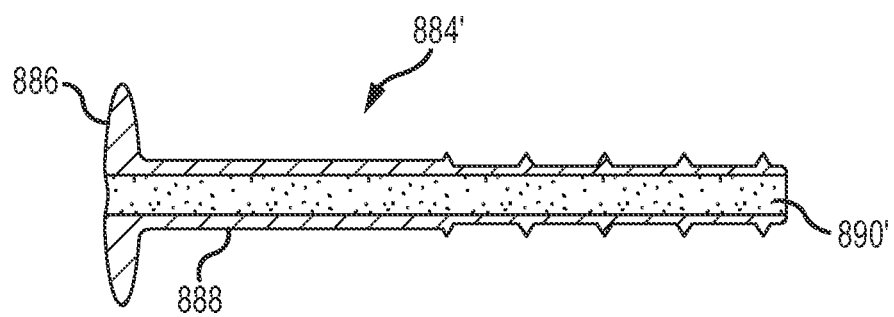
FIG. 17 is a sectional view of an embodiment of a modified implant device form prepared by modification of the preliminary implant device form of FIG. 16.

Reference is now made to FIGS. 16 and 17 in relation to an example of modifying a preliminary internal passage structure of a preliminary implant device form to apply a lubricity agent to the internal passage. FIG. 16 shows an initial implant device form 884 including a head 886 and a conduit 888 and having a preliminary internal passage 890 passing through the head 886 and the conduit 888. The preliminary implant device form 884 is illustrated as having features of the implant device of FIG. 4, but it could alternatively be of a different design, for example with one or more features shown in any of FIG. 2-3, 6-15 or 18-26. FIG. 17 shows a modified implant device form 884' with a modified internal passage structure 890' following formation of a thin layer of or including a lubricity agent. Such a thin layer of lubricity material may be formed, for example, by casting a film of or including the lubricity agent or precursor therefore onto the walls of the preliminary internal passage 890 and then curing the cast film as necessary to form a final coating with high lubricity. Such a lubricity agent may, for example, be a fluorosilicone polymer or a very smooth silicone film (e.g., similar to layers 876 and 880). One example silicone material for such a smooth film is a film formed by reaction of ethyltriacetoxysilane. As another example, the layers of lubricity material may be deposited by chemical vapor deposition, for example a poly(p-xylylene) polymer (e.g., Parylene N or Parylene C). An internal passage could also be treated to apply an antimicrobial agent, with or without applying a lubricity agent, similar to as described in relation to FIGS. 14-15.

Figure 18:
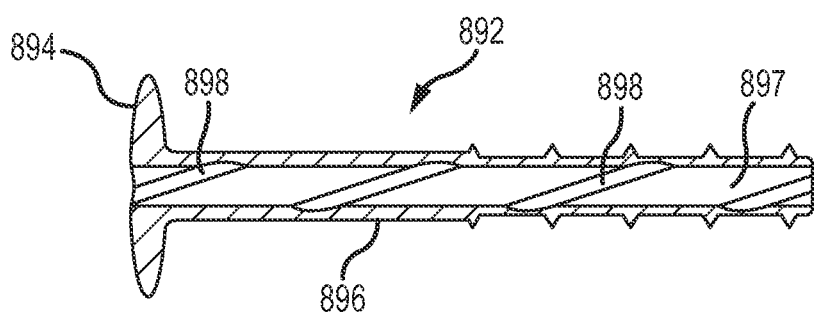
FIG. 18 is a sectional view of an embodiment of an implant device.

Reference is now made to FIG. 18 showing a cross-section of an implant device 892 having a head 894 and a conduit 896 and with an internal passage 897 extending through the head 894 and the conduit 896. The implant device 892 is illustrated with features of the implant device of FIG. 4, but it could be of a different design, for example including one or more features shown in any of FIG. 2-3, 6-17 or 19-26. The internal passage 897 of the implant device 892 has a surface geometry including rifling 898 in the form of a spiraling recess extending the along the length of the internal passage 897.

Figure 19:
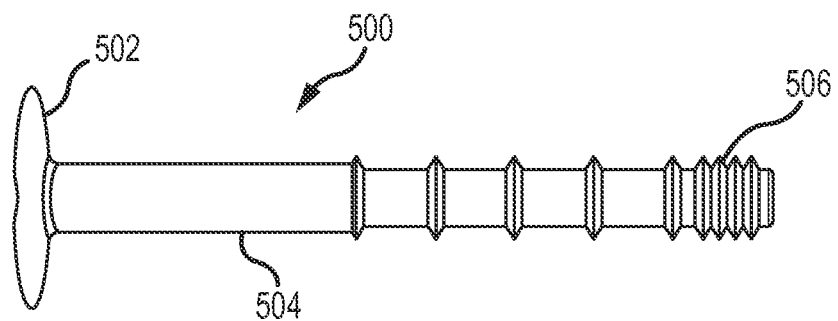
FIGS. 19 and 20 are side views of an embodiment of an implant device including a conduit extension portion in a fully contracted and fully extended configuration, respectively.
Figure 20:
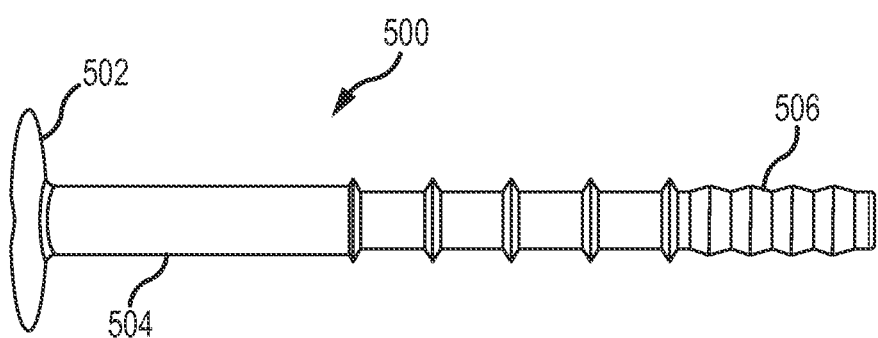
Figure 21:
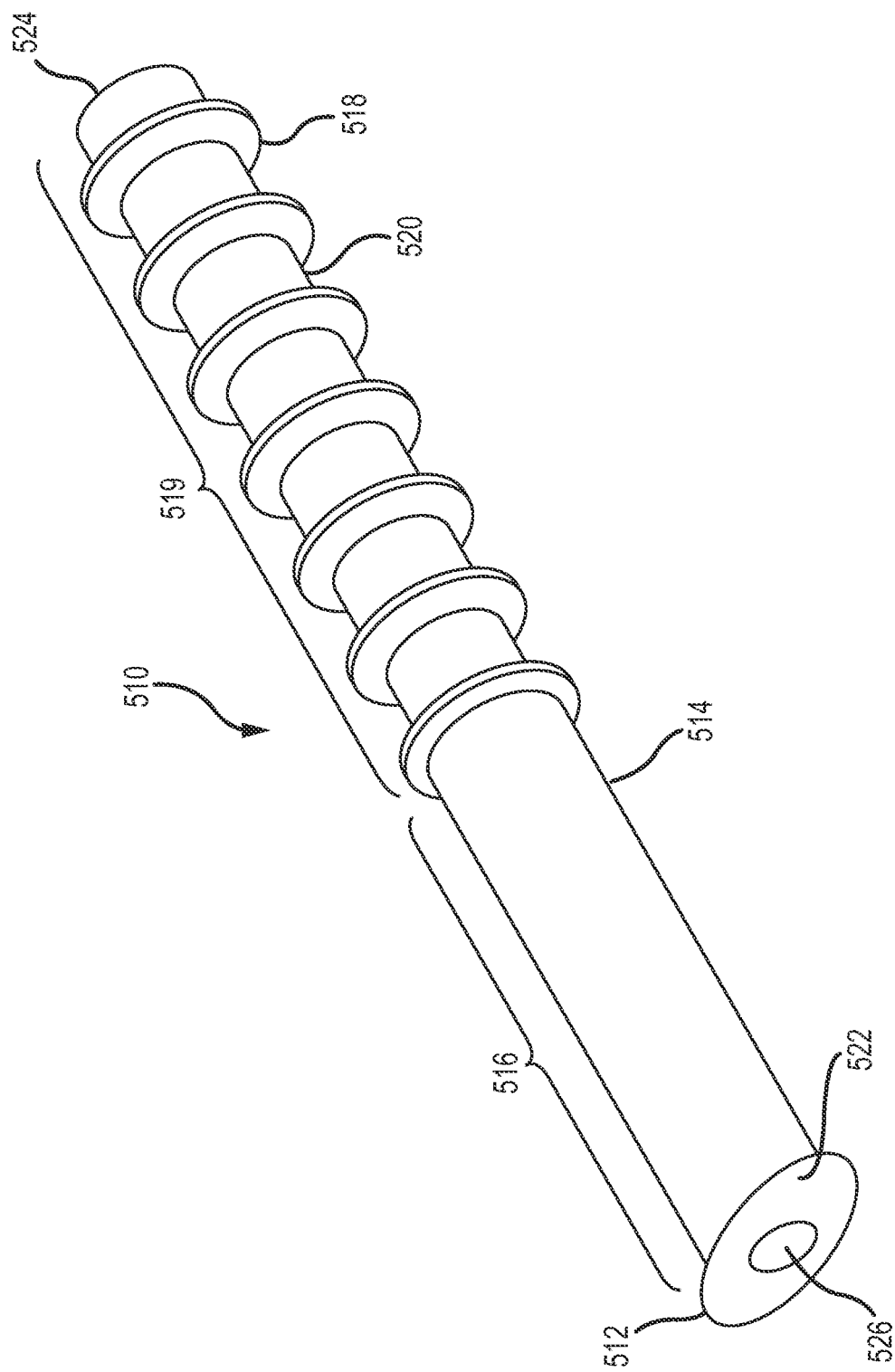
FIGS. 21-26 illustrate another embodiment of an implant device.
Figure 22:
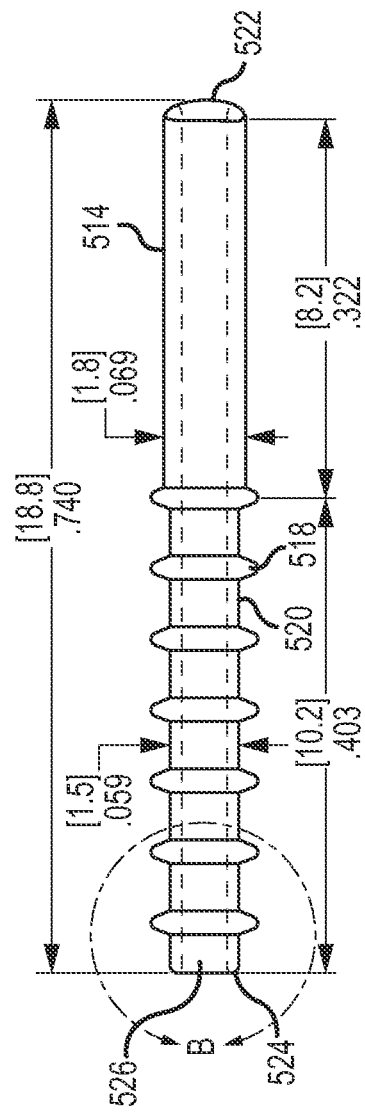
Figure 23:
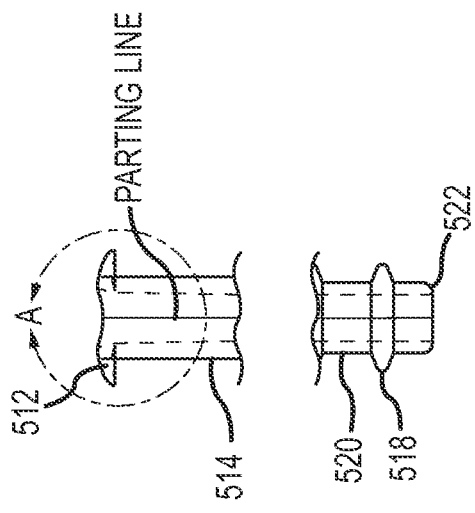
Figure 24:
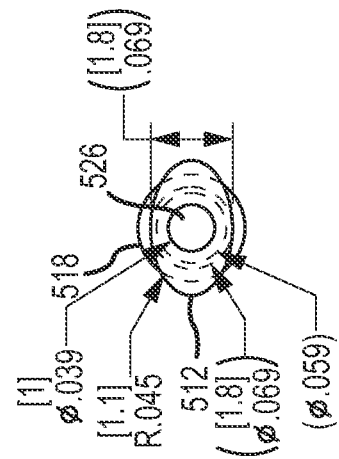
Figure 25:
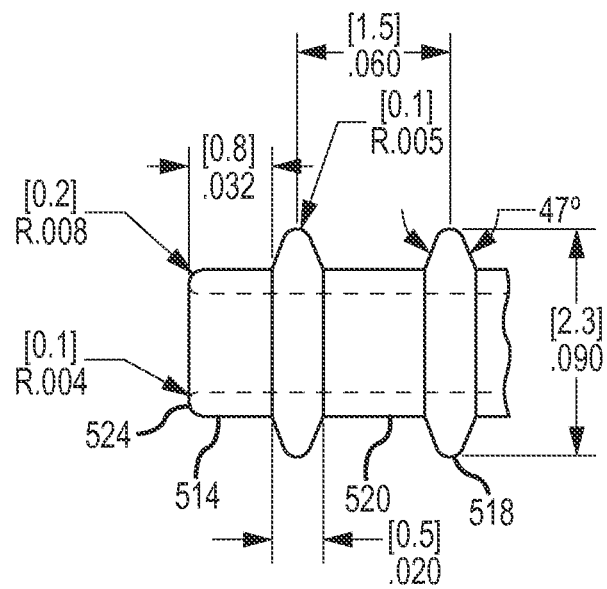
Figure 26:
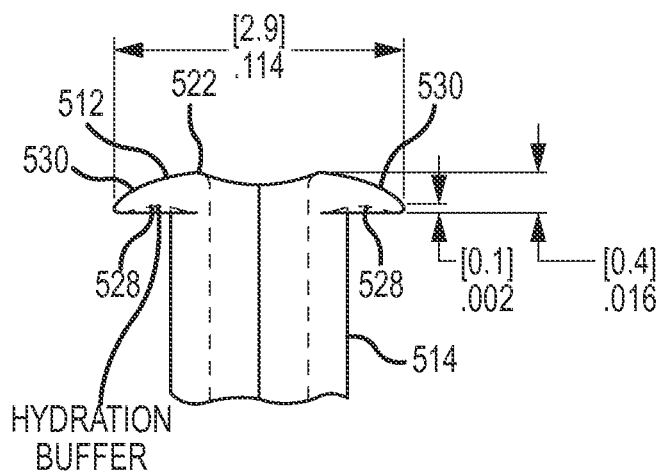

Reference is now made to FIGS. 19 and 20 illustrating one example of an extension portion on a conduit that is extendable and collapsible, or contractible, to lengthen and shorten, respectively, a longitudinal length of a distal portion of a conduit of an implant device. As shown in FIGS. 19 and 20, an implant device 500 includes a head 502 and a conduit 504, and which may have a design similar to that or including any features of an implant device shown in any of FIG. 2-18 or 21-26, except that on a distal portion of the conduit 504, the implant device 500 includes an extension portion 506 of a pleated, or accordion, structure that may be extended and contracted to lengthen and shorten, respectively, a distal portion of the conduit 504 that is to be disposed within the paranasal sinus when the implant device 500 is implanted. The extension portion 506 is shown in a fully contracted, or collapsed, configuration in FIG. 19 and in a fully extended configuration in FIG. 20.

FIGS. 21-26 show another embodiment of a paranasal sinus access implant device. The implant device 510 has a head 512 and a conduit 514 with a first longitudinal portion 516 having a larger minimum wall thickness and a second longitudinal portion 519 having a smaller minimum wall thickness. The implant device 510 has seven anchor protrusions 518 in the form of circumferential ridges and recess areas 520 between pairs of adjacent ridges. The implant device 510 has a proximal end 522 and a distal end 524 and an internal passage 526 that extends from the proximal end 522 through the head 512 and the conduit 514 to the distal end 524. Various details and dimensions for the implant device 510 are shown in FIGS. 22-26. Dimensions are shown in FIGS. 22-26 in inches and in millimeters, with the dimensions in millimeters being in brackets. As will be appreciated, compared to the implant device 800 of FIG. 4, the implant device 510 of FIGS. 21-26 has more circumferential ridges with a closer spacing between the ridges and a smaller head, and with the head 512 having concave surfaces 528 on the distal side of the flanged portions of the head 512 and having convex surfaces 530 on the proximal side of the flanged portions of the head 512 (seen best in FIG. 26). The concave surfaces 528 on each of the flanged portions of the head are in the form of a cup-shaped depression that may trap and hold liquid between soft tissue (e.g., in the orbit) and the concave surfaces 528 to maintain a hydration buffer between the flanged portions of the head 512 and the soft tissue when the implant device is implanted.

In one variation of the implant device 510, the conduit 514, or a portion of the conduit 514, may be made of a radiopaque material. For example a polymer composition containing a filler of particles of a radiopaque material. For example the conduit 514 may be made of a 70-90 Shore A durometer silicone containing 20-30% of barium sulfate particles. The head 512 may be made of a similar polymer material, but not containing radiopaque material, so that the head 512 may be clear and transparent. The head 512, conduit 514 and/or internal passage 526 may be modified in any manner as discussed previously, for example with respect to any one or more of FIGS. 9-17.

Figure 27:
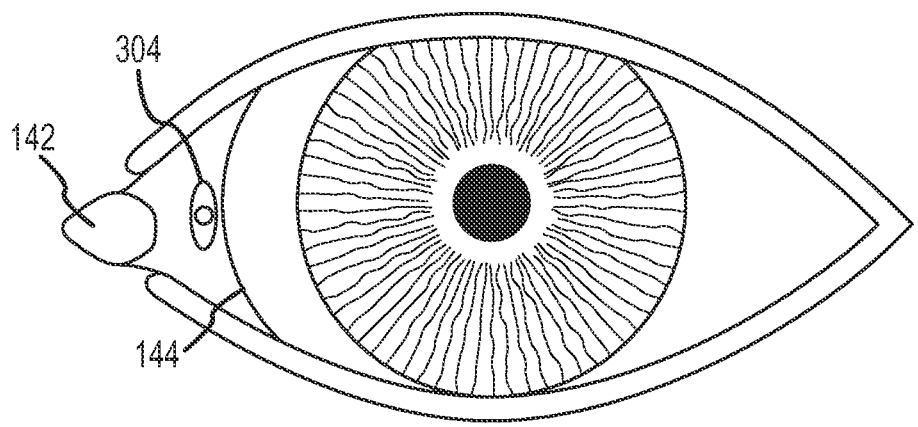
FIG. 27 is an illustration showing an embodiment for placement of an implant device with a head of the implant device located within the lacrimal apparatus in the orbit.

FIG. 27 shows an example of an implant device with a conduit passing through a fistula formed from the orbit subconjunctivally between the lacrimal caruncle 142 and the plica semilunaris 144, and showing an example location for the head 304 of the implant device disposed in the orbit, shown for example between the lacrimal caruncle 142 and the plica semilunaris 144.

Figure 28:
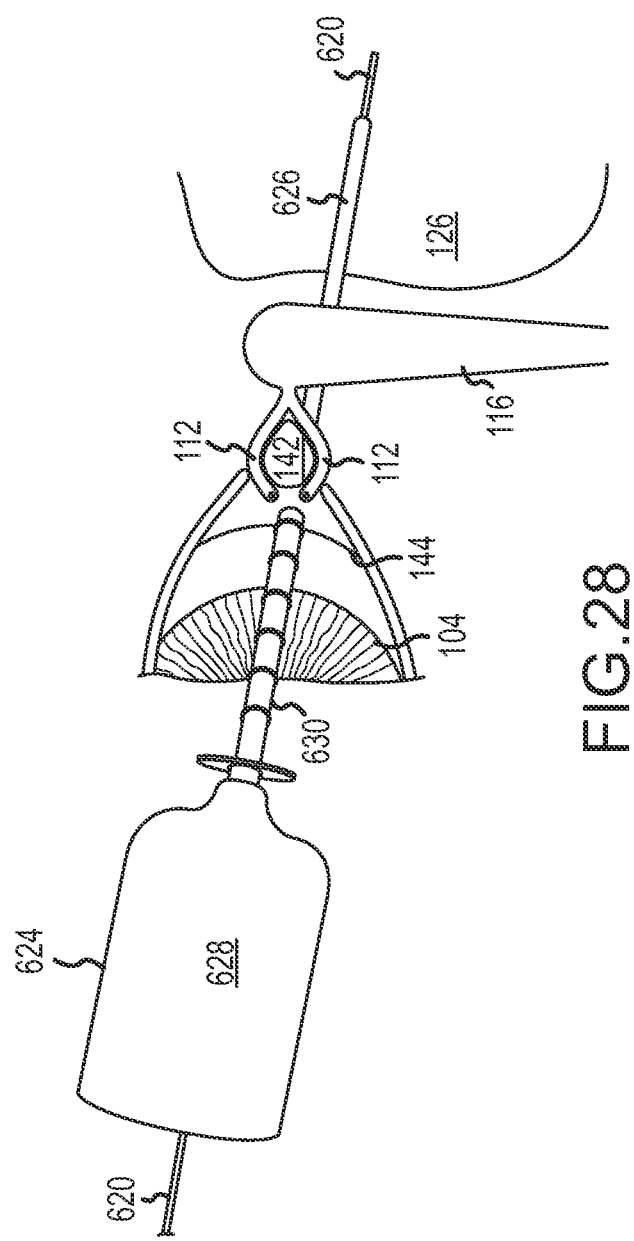
FIG. 28 is an illustration showing use of a surgical tool, in the form of a carrier tool, for implantation of an implant device during a surgical procedure.
Figure 29:
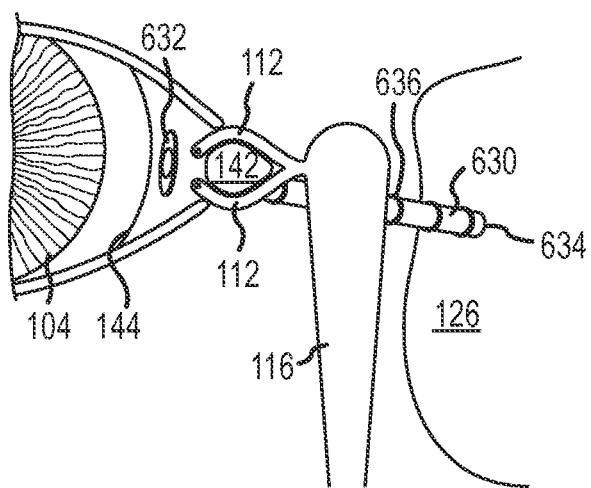
FIG. 29 is an illustration showing placement of an implant device following implantation during a surgical procedure.

FIGS. 28 and 29 show an example implementation of an implant device 630 to fluidly connect between the lacrimal apparatus in the orbit and the ethmoid sinus 126. To facilitate implantation, the implant device 630 is mounted on a surgical tool, in the form of an implant tool 624. The implant tool may also be referred to as a carrier tool. The implant tool 624 includes a hollow working member 626 and a hand-manipulable handle 628. The implantation tool 624 is shown with the hollow working member 626 advanced through a previously formed fistula between the lacrimal apparatus in the orbit and the paranasal sinus 126. The working member 626 may also be referred to as a carrier member. The implant tool 624 includes an internal passage passing through the handle 628 and the hollow working member 626. As shown in FIG. 28, a guide wire 620 has been threaded through the internal passage of the implant tool 624 to guide the hollow working member 626 to and through the fistula and into the ethmoid sinus 126. The implant device 630 is mounted on the hollow working member 626 of the implant tool 624. FIG. 28 shows the implant tool 624 advanced to a point where the distal end of the implant device 630 is in the vicinity of the proximal end of the fistula opening into the conjunctival sac. From this position, the implant device 630 may be advanced into the fistula with a head of the implant device 630 disposed adjacent the conjunctiva in the conjunctival sac and a distal end of the implant device 630 extending into the ethmoid sinus 626. For example, a surgeon may slide the implant device 630 down the hollow working member 626 for placement through the fistula for implantation or the surgeon may advance the handle 628 to have the handle push the implant device 630 into the fistula for implant placement. The outside diameter of the hollow working member 626 may be sized to closely fit within the inside diameter of the implant device 630 to help prevent the implant device 630 from bunching-up and laterally deforming as the implant device is pushed into the fistula. The handle 628 and the hollow working member 626 form a carrier for the implant device 630. The handle 628 may be retracted and the hollow working member 626 disengaged from the implant device 630 after the implant device has been appropriately positioned for implantation through the fistula. FIG. 29 shows the implant device 630 as implanted and following disengagement of the hollow working member 626 of the implantation tool 624. As implanted, a head 632 at the proximal end of the implant device 630 is located adjacent the conjunctiva in the conjunctival sac within the lacrimal apparatus in the orbit, and the conduit passes through the fistula across tissue including conjunctiva and a wall of the ethmoid bone in which the ethmoid sinus 126 is located. A distal end 634 of the implant device 630 is located in the ethmoid sinus 126. Some anchor protrusions 636 of the conduit of the implant device 630 are disposed within the fistula to engage tissue and help anchor the implant device 630. The implant device 630 may be used to provide access to the ethmoid sinus 126 to perform medical procedures or treatments, for example to administer a treatment composition to the ethmoid sinus or to aspirate fluid from the ethmoid sinus.

A variety of medical treatments and procedures may be performed through a paranasal sinus access implant device implanted to provide access to a paranasal sinus. Fluid treatment compositions may be administered to a paranasal sinus through the implant device. Fluid may be aspirated from a paranasal sinus through the implant device. One or more medical devices may be inserted into the paranasal sinus through the implant device.

Some example implementation combinations, and for various types of implementation applications, which may be the subject of claims with or without additional features as disclosed above, are disclosed as follows:

1. A paranasal sinus access implant device useful for implantation in a human to fluidly connect a lacrimal apparatus to a paranasal sinus through a fistula formed between the lacrimal apparatus and the paranasal sinus, the implant device comprising:

a proximal end at a first longitudinal end of the device to be disposed in the lacrimal apparatus when the device is implanted and a distal end at a second longitudinal end of the device to be disposed in the paranasal sinus when the device is implanted;

a length longitudinally along the implant device between the proximal end and the distal end in a range of from 2 millimeters to 50 millimeters;

a conduit, located between the proximal end and distal end, to be disposed through a fistula between the lacrimal apparatus and the paranasal sinus when the device is implanted;

a head located proximal of the conduit, to be disposed in the lacrimal apparatus when the device is implanted;

an internal passage through the head and the conduit, to provide a fluid communication path between the lacrimal apparatus and the paranasal sinus when the device is implanted, the internal passage having a width through at least a portion of the conduit in a range of from 0.25 millimeter to 5 millimeters;

wherein the implant device comprises at least one of the following:

(i) the conduit comprises a first material having a first hardness and the head comprises a second material having a second hardness that is smaller than the first hardness;

(ii) the conduit comprises a distal portion to be disposed in the paranasal sinus when the device is implanted, the distal portion of the conduit comprising a structural portion of a first material having a first hardness and a skin portion supported by the structural portion, the skin portion including an a second material having a second hardness that is smaller than the first hardness;

(iii) the head comprises a structural portion of a first material having a first hardness and a skin portion supported by the structural portion, the skin portion including a second material having a second hardness that is smaller than the first hardness;

(iv) the head has an exposed surface of a second material having a hardness of not larger than Shore A 45 durometer;

(v) the head comprises an exposed surface of a second material, the exposed surface having an average roughness (Ra) of not larger than 200 nanometers, or even not larger than 50 nanometers;

(vi) the conduit comprises a distal portion to be disposed in the paranasal sinus when the device is implanted, the distal portion of the conduit comprising an exposed surface of a second material, the exposed surface having an average roughness (Ra) of not larger than 200 nanometers, or even not larger than 50 nanometers;

(vii) the head comprises an exposed surface of a second material comprising a wetting agent to impart hydrophilicity to the exposed surface;

(viii) the conduit comprises a distal portion to be disposed in the paranasal sinus when the device is implanted, the distal portion of the conduit comprising an exposed surface of a second material comprising a wetting agent to impart hydrophilicity to the exposed surface;

(ix) the head comprises an exposed surface of a second material comprising an antimicrobial agent;

(x) the conduit comprises a distal portion to be disposed in the paranasal sinus when the device is implanted, the distal portion of the conduit comprising an exposed surface of a second material comprising an antimicrobial agent;

(xi) the head comprises a distal side having a concave surface disposed toward the distal end of the device;

(xii) the internal passage has a surface of a second material comprising a lubricity agent;

(xiii) at least a portion of the conduit is of a radiopaque material;

(xiv) the internal passage has a surface geometry comprising rifling;

(xv) the conduit comprises a distal extension portion that is extendable and collapsible to lengthen and shorten a longitudinal length of a distal portion of the conduit disposed in the paranasal sinus when the device is implanted; and (xvi) the implant device is packaged in sterile packaging in contact with a storage liquid.

2. An implant device according to example implementation combination 1, comprising one or more of (i)-(iii) and wherein the first material has a hardness in a range of from Shore A 50 durometer to Shore A 100 durometer.

3. An implant device according to example implementation combination 2, wherein the first material comprises a silicone material.

4. An implant device according to example implementation combination 3, wherein the silicone material comprises polydimethylsiloxane.

5. An implant device according to example implementation combination 2, wherein the first material comprises a polyurethane.

6. An implant device according to any one of example implementation combinations 2-5 wherein the first material has a hardness that is at least 20 Shore A durometer units larger than a hardness of the second material.

7. An implant device according to any one of example implementation combinations 1-6, comprising one or more of (i)-(x) and wherein the second material has a hardness in a range of from Shore A 5 durometer to Shore A 45 durometer.

8. An implant device according to example implementation combination 7, wherein the second material comprises a silicone material.

9. An implant device according to example implementation combination 7, wherein the second material comprises a silicone hydrogel.

10. An implant device according to any one of example implementation combinations 7-9, comprising one or both of items (ii) and (iii) and wherein the skin portion has a depth below the exposed surface in a range of from 10 microns to 200 microns.

11. An implant device according to any one of example implementation combinations 7-10, comprising one or both of (v) and (vi) and wherein the average roughness (Ra) is in a range of from 1 nanometer to 20 nanometers.

12. An implant device according to any one of example implementation combinations 7-11, comprising one or both of (vii) and (viii) and wherein the wetting agent is selected from the group consisting of polyvinylpyrrolidone, polyethylene glycol, hyaluronic acid and combinations thereof.

13. An implant device according to any one of example implementation combinations 7-12, comprising one or both of (ix) and (x) and wherein the antimicrobial agent comprises a member selected from the group consisting of silver, poly(ethylene oxide), polyethylene glycol and combinations thereof.

14. An implant device according to any one of example implementation combinations 7-13, comprising one or both of (ix) and (x) and wherein the antimicrobial agent comprises an antimicrobial peptide.

15. An implant device according to any one of example implementation combinations 7-14, comprising one or both if (ix) and (x) and wherein the second material comprises a polymeric material impregnated with the antimicrobial agent.

16. An implant device according to any one of example implementation combinations 1-15, comprising one or more of (i)-(iii), wherein a third material is disposed between the first material and the second material, the third material having a third hardness that is smaller than the first hardness and larger than the second hardness.

17. An implant device according to example implementation combination 16, wherein the third hardness is at least 10 Shore A durometer units smaller than the first hardness and the second hardness is at least 10 Shore A durometer units smaller than the third hardness.

18. An implant device according to either one of example implementation combinations 16 or claim 17, wherein the third harness is in a range of from Shore A 20 durometer to Shore A 50 durometer.

19. An implant device according to any one of example implementation combinations 16-18, wherein the third material comprises a silicone material.

20. An implant device according to any one of example implementation combinations 1-19, comprising (xii) and wherein the lubricity agent is selected from the group consisting of a fluorosilicone, a smooth silicone film having an average roughness Ra of not larger than 50 nanometers, a poly (p-xylylene) and combinations thereof 21. An implant device according to any one of example implementation combinations 1-20, comprising (xii) and wherein the lubricity agent is in the form of a coating on walls of the internal passage.

22. An implant device according to example implementation combination 21, wherein the coating has a thickness in a range of from 1 micron to 50 microns.

23. An implant device according to any one of example implementation combinations 1-22, comprising (xiii) and wherein the radiopaque material comprises a polymeric material mixed with a radiopaque additive.

24. An implant device according to example implementation combination 23, wherein the radiopaque additive is selected from the group consisting of barium sulfate, titanium metal, tantalum metal, gold metal, platinum metal, iodine, bismuth subcarbonate, bismuth trioxide, bismuth oxychloride, tungsten metal and combinations thereof.

25. An implant device according to either one of example implementation combination 23 or example implementation combination 24, wherein the radiopaque material comprises the radiopaque additive in an amount in a range of from 1 weight % to 90 weight %.

26. An implant device according to any one of example implementation combinations 1-25, comprising (xiii) and wherein at least a portion of the conduit has a radiodensity in a range of from 100 Hounsfield units to 900 Hounsfield units.

27. An implant device according to any one of example implementation combinations 1-26, comprising (xiii) and wherein the conduit has a radiopaque portion made of the radiopaque material, the radiopaque portion of the conduit extending for at least 5 millimeters of a longitudinal length of the conduit.

28. An implant device according to example implementation combination 27, wherein a proximal end of the radiopaque portion of the conduit is spaced at least 0.5 millimeter from the head.

29. An implant device according to example implementation combination 27, wherein the radiopaque portion extends over the entire longitudinal length of the conduit.

30. An implant device according to any one of example implementation combinations 1-29, comprising (xiii) and wherein the head does not contain a radiopaque additive.

31. An implant device according to any one of example implementation combinations 1-30, comprising (xiii) and wherein at least a portion of the head has a radiodensity of no larger than 50 Hounsfield units.

32. An implant device according to example implementation combination 31, wherein the entire head has a radiodensity of not larger than 75 Hounsfield units.

33. An implant device according to any one of example implementation combinations 1-32, wherein the head has a length dimension and a width dimension transverse to the length dimension with a ratio of the length dimension to the width dimension in a range of from 1.5 to 4.

34. An implant device according to any one of example implementation combinations 1-33, wherein the head has a length dimension and a width dimension transverse to the length dimension, the length dimension being in a range of from 3 millimeters to 8 millimeters.

35. An implant device according to any one of example implementation combinations 1-34, wherein an exterior of the conduit comprises an anchoring surface feature including protrusion areas and recess areas.

36. An implant device according to either one of example implementation combination 34 or example implementation combination 35, wherein the protrusion areas are on a longitudinal portion of the conduit having a proximal end that is disposed at least 3 millimeters distal of the head.

37. An implant device according to any one of example implementation combinations 1-36, wherein the length between the proximal end and the distal end of the device is in a range of from 8 millimeters to 30 millimeters.

38. An implant device according to any one of example implementation combinations 1-37, wherein the extension portion comprises a pleated structure.

39. A method of making a paranasal sinus access implant device according to any one of example implementation combinations 1-38 and 78-83, wherein the paranasal sinus access implant device comprises at least one said second material, the method comprising:
providing a preliminary form including a preliminary head structure and a preliminary conduit structure; and
forming at least one said second material supported by one or both of the preliminary head structure and the preliminary conduit structure.

40. A method according to example implementation combination 39, wherein the implant device comprises (i), the preliminary conduit structure of the preliminary form comprises the first material as recited in (i) and the forming at least one said second material comprises:
forming over at least a portion of the preliminary head structure a said second material as recited in (i) with the exposed surface as recited in (i).

41. A method according to either one of example implementation combination 39 or example implementation combination 40, wherein the implant device comprises (ii), the preliminary conduit structure comprises the first material as recited in (ii) and the forming at least one said second material comprises:
forming over at least a portion of said first material as recited in (ii) of the preliminary conduit structure a said second material as recited in (ii) with the exposed surface as recited in (ii).

42. A method according to any one of example implementation combinations 39-41, wherein the implant device comprises (iii) and the preliminary head structure of the preliminary form comprises the first material as recited in (iii), and the forming at least one said second material comprises:
forming over at least a portion of said first material as recited in (iii) of the preliminary head structure a said second material as recited (iii) with the exposed surface as recited in (iii).

43. A method according to any one of example implementation combinations 39-42, wherein the implant device comprises (iv) and the forming at least one said second material comprises:
forming over at least a portion of the preliminary head structure a said second material as recited in (iv) with the exposed surface recited in (iv).

44. A method according to any one of example implementation combinations 39-43, wherein the implant device comprises (v) and the forming at least one said second material comprises:
forming over at least a portion of the preliminary head structure a said second material as recited in (v) with the exposed surface as recited in (v).

45. A method according to any one of example implementation combinations 39-44, wherein the implant device comprises (vi) and the forming at least one said second material comprises:
forming over at least a portion of the preliminary conduit structure a said second material as recited in (vi) with the exposed surface as recited in (vi).

46. A method according to any one of example implementation combinations 39-45, wherein the implant device comprises (vii) and the forming at least one said second material comprises:
forming over at least a portion of the preliminary head structure a said second material as recited in (vii) with the exposed surface as recited in (vii).

47. A method according to any one of example implementation combinations 39-46, wherein the implant device comprises (viii) and the forming at least one said second material comprises:
forming over at least a portion of the preliminary conduit structure a said second material as recited in (viii) with the exposed surface as recited in (viii).

48. A method according to any one of example implementation combinations 39-47, wherein the implant device comprises (ix) and the forming at least one said second material comprises:
forming over at least a portion of the preliminary head structure a said second material as recited in (ix) with the exposed surface as recited in (ix).

49. A method according to any one of example implementation combinations 39-48, wherein the implant device comprises (x) and the forming at least one said second material comprises:
forming over at least a portion of the preliminary conduit structure a said second material as recited in (x) with the exposed surface as recited in (x).

50. A method according to any one of example implementation combinations 39-49, wherein paranasal sinus access implant device comprises (xii), the preliminary form comprises a preliminary internal passage through the preliminary conduit structure and the preliminary head structure and the method comprises:
forming over a wall of the preliminary internal passage a said second material as recited in (xii) with the exposed surface recited in (xii).

51. A method according to any one of example implementation combinations 39-50, wherein the providing a preliminary form comprises:
molding a polymeric composition in the shape of the preliminary form.

52. A method according to example implementation combination 51, wherein the molding comprises a molding technique selected from the group consisting of injection molding, compression molding and transfer molding.

53. A method according to any one of example implementation combinations 39-52, wherein the providing a preliminary form comprises:
extruding a first preliminary form and then molding additional features onto the first preliminary form to form a second preliminary form.

54. A method according to only one of example implementation combinations 51-53, wherein the providing a preliminary form comprises:
removing flash from a molded article resulting from the molding.

55. A method according to any one of example implementation combinations 39-54, wherein the forming at least one said second material comprises:

dip molding a said second material over at least a portion of said preliminary head structure.

56. A method according to any one of example implementation combinations 39-55, wherein the forming at least one said second material comprises:
dip molding a said second material over at least a portion of said preliminary conduit structure.

57. A method according to either one of example implementation combination 55 or example implementation combination 56, wherein the dip molding comprises:
applying at least a portion of the preliminary form with a precursor solution comprising at least one precursor for a said second material;
drying the applied precursor solution to leave the at least one precursor on the preliminary form; and
curing the at least one precursor to form a polymeric composition of a said second material.

58. A method according to example implementation combination 57, wherein the polymeric composition is a thermoset composition, and the curing comprises heating the at least one precursor on the preliminary form.

59. A method according to any one of example implementation combinations 39-58, wherein the forming at least one said second material comprises:
forming an intermediate material over at least a portion of one or both of the preliminary head structure and a preliminary conduit structure; and
after the forming an intermediate material, forming the second material over at least a portion of the preliminary material.

60. A method according to any one of example implementation combinations 39-59, wherein the forming at least one said second material comprises:
forming a preliminary material over at least a portion of one or both of the preliminary head structure and a preliminary conduit structure; and
after the forming a preliminary material, modifying the preliminary material to form a said second material.

61. A method according to example implementation combination 60, wherein the modifying the preliminary material comprises adding to the preliminary material an additive material.

62. A method according to example implementation combination 61, wherein the additive material is selected from the group consisting of a said wetting agent, a said antimicrobial agent and combinations thereof.

63. A method of treating a condition of a paranasal sinus of a patient having the implant device of any one of example implementation combinations 1-38 and 78-83 implanted to fluidly connect a lacrimal apparatus of the patient to a paranasal sinus of the patient, the method comprising the administering a treatment composition to the patient to be delivered to the paranasal sinus through the internal passage of the implant device.

64. A product, comprising:
a paranasal sinus access implant device;
sterile storage liquid in contact with the implant device;
sterile packaging, wherein the implant device and the storage liquid are disposed within the sterile packaging.

65. A product according to example implementation combination 64, wherein the implant device comprises:
a proximal end at a first longitudinal end of the device to be disposed in the lacrimal apparatus when the device is implanted and a distal end at a second longitudinal end of the device to be disposed in the paranasal sinus when the device is implanted;
a length longitudinally along the implant device between the proximal end and the distal end in a range of from 2 millimeters to 50 millimeters.
a conduit, located between the proximal end and distal end, to be disposed through a fistula between the lacrimal apparatus and the paranasal sinus when the device is implanted;
a head located proximal of the conduit, to be disposed in the lacrimal apparatus when the device is implanted;
an internal passage through the head and the conduit, to provide a fluid communication path between the lacrimal apparatus and the paranasal sinus when the device is implanted, the internal passage having a width through at least a portion of the conduit in a range of from 0.25 millimeter to 5 millimeters.

66. A product according to either one of example implementation combination 64 and example implementation combination 65, wherein all exterior surfaces of the implant device are in contact with the storage liquid.

67. A product according to any one of example implementation combinations 64-66, wherein all surfaces of the implant device are in contact with the storage liquid.

68. A product according to any one of example implementation combinations 64-67, wherein the implant device is disposed within the sterile packaging in a reservoir of the storage liquid.

69. A product according to any one of example implementation combinations 64-68, wherein the storage liquid comprises an aqueous liquid.

70. A product according to any one of example implementation combinations 64-69, wherein the storage liquid comprises a buffer solution.

71. A product according to any one of example implementation combinations 64-70, wherein the storage liquid comprises a wetting agent.

72. A product according to example implementation combination 71, wherein the wetting agent comprises hyaluronic acid.

73. A product according to any one of example implementation combinations 64-72, wherein the product comprises a plurality of said implant devices and the sterile packaging comprises a plurality of sealed compartments each having disposed therein a said implant device in contact with a said storage liquid.

74. A product according to any one of example implementation combinations 64-73, wherein the implant device is according to any one of example implementation combinations 1-38 and 78-83.

75. A product according to example implementation combination 74, wherein the implant device comprises (xvi).

76. A method for implanting a paranasal sinus access implant device to fluidly connect a lacrimal apparatus and a paranasal sinus, the method comprising:
from the product of any one of example implementation combinations 64-75, removing the implant device from the sterile packaging; and
implanting the implant device with a proximal end disposed in the lacrimal apparatus and a distal end disposed in the paranasal sinus to fluidly connect the lacrimal apparatus and the paranasal sinus through an internal passage of the implant device.

77. A method according to example implementation combination 76, wherein after the removing and at the commencement of the implanting, at least a portion of the implant device is covered with at least a residual portion of the storage liquid.

78. An implant device according to any one of example implementation combinations 1-38, comprising a said exposed surface having has an area of at least 1 square millimeter.

79. An implant device according to any one of example implementation combinations 1-38 and 78, comprising a said exposed surface on an exterior of the distal portion of the conduit, which distal portion of the conduit is to be disposed in the paranasal sinus when the implant device is implanted.

80. An implant device according to example implementation combination 79, wherein a said exposed surface extends for at least 2 millimeters along a longitudinal length of the conduit adjacent to the distal end.

81. An implant device according to either one of example implementation combination 77 and example implementation combination 80, wherein a said exposed surface extends entirely around an exterior circumference of the distal portion of the conduit.

82. An implant device according to any one of example implementations 1-38 and 78-81, wherein the Ra is as determined by optical non-contact profilometry or by laser profilometry.

83. An implant device according to any one of example implementations 1-38 and 78-82, wherein the head comprises flanged portions having a refractive index across the thickness of the flanged portions of not larger than 1.5.

84. An implant device according to any one of example implementation combinations 1-38 and 78-83, wherein the implant device is implanted in a human and fluidly connects a location in the lacrimal apparatus with a paranasal sinus.

The foregoing discussion of the invention and different aspects and different example implementation combinations thereof has been presented for purposes of illustration and description. The foregoing is not intended to limit the invention to only the form or forms specifically disclosed herein. Consequently, variations and modifications commensurate with the above teachings, and the skill or knowledge of the relevant art, are within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art. Although the description of the invention has included description of one or more possible implementations and certain variations and modifications, other variations and modifications are within the scope of the invention, e.g., as may be within the skill and knowledge of those in the art after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Furthermore, any feature described or claimed with respect to any disclosed implementation may be combined in any combination with one or more of any other features of any other implementation or implementations, to the extent that the features are not necessarily technically incompatible, and all such combinations are within the scope of the present invention.

The terms "comprising", "containing", "including" and "having", and grammatical variations of those terms, are intended to be inclusive and nonlimiting in that the use of such terms indicates the presence of some condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or the appropriate grammatical variation of such narrower terms). For example, a statement that some thing "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term "at least a portion" means all or a portion that is less than all. The term "at least a part" means all or a part that is less than all.

The features in the drawings are shown for illustration purposes and to generally show relative positioning and interaction, and the features shown are not necessarily to scale.

What is claimed is:

1. A paranasal access implant device for implantation in a human to fluidly connect a lacrimal apparatus to a paranasal sinus through a fistula formed between the lacrimal apparatus and the paranasal sinus, the implant device comprising:
  a proximal end at a first longitudinal end of the device to be disposed in the lacrimal apparatus when the device is implanted and a distal end at a second longitudinal end of the device to be disposed in the paranasal sinus when the device is implanted;
  a length longitudinally along the implant device between the proximal end and the distal end in a range of from 8 millimeters to 50 millimeters;
  a conduit, located between the proximal end and distal end, to be disposed through a fistula between the lacrimal apparatus and the paranasal sinus when the device is implanted, the conduit comprising a distal portion to be disposed in the paranasal sinus when the implant device is implanted;
  a head located proximal of the conduit, to be disposed in the lacrimal apparatus when the device is implanted; and
  an internal passage through the head and the conduit, to provide a fluid communication path between the lacrimal apparatus and the paranasal sinus when the device is implanted, the internal passage having a width through at least a portion of the conduit in a range of from 0.25 millimeter to 5 millimeters;
  and wherein:
    at least one of the head and the distal portion of the conduit comprises an exposed surface of exposed material, the exposed surface having an average roughness (Ra) in a range of from 1 nanometer to 200 nanometers;
the Ra is in a range of from 1 nanometer to 50 nanometers over a continuous surface area of at least 2 square millimeters on the head;
the conduit comprises a first material having a first hardness and the head comprises a second material having a second hardness that is smaller than the first hardness;
the head comprises a structural portion of the first material and a skin portion supported by the structural portion, the skin portion including the second material;
the skin portion has a depth below the exposed surface in a range of from 10 microns to 200 microns;
the first material has a hardness in a range of from Shore A 50 durometer to Shore A 100 durometer; and
the second material comprises a silicone material or a silicone hydrogel.

2. A paranasal sinus access implant device for implantation in a human to fluidly connect a lacrimal apparatus to a paranasal sinus through a fistula formed between the lacrimal apparatus and the paranasal sinus, the implant device comprising:
a proximal end at a first longitudinal end of the device to be disposed in the lacrimal apparatus when the device is implanted and a distal end at a second longitudinal end of the device to be disposed in the paranasal sinus when the device is implanted;
a length longitudinally along the implant device between the proximal end and the distal end in a range of from 8 millimeters to 50 millimeters;
a conduit, located between the proximal end and distal end, to be disposed through a fistula between the lacrimal apparatus and the paranasal sinus when the device is implanted, the conduit comprising a distal portion to be disposed in the paranasal sinus when the implant device is implanted;
a head located proximal of the conduit, to be disposed in the lacrimal apparatus when the device is implanted; and
an internal passage through the head and the conduit, to provide a fluid communication path between the lacrimal apparatus and the paranasal sinus when the device is implanted, the internal passage having a width through at least a portion of the conduit in a range of from 0.25 millimeter to 5 millimeters;
and wherein:
at least one of the head and the distal portion of the conduit comprises an exposed surface of exposed material, the exposed surface having an average roughness (Ra) in a range of from 1 nanometer to 200 nanometers;
the Ra is in a range of from 1 nanometer to 50 nanometers over a continuous surface area of at least 2 square millimeters on the head;
at least a portion of the conduit is of a radiopaque material having a radiodensity in a range of from 100 Hounsfield units to 900 Hounsfield units;
the conduit has a radiopaque portion made of the radiopaque material, the radiopaque portion of the conduit extending for at least 5 millimeters of a longitudinal length of the conduit; and
the head comprises flanged portions having a refractive index across the thickness of the flanged portions of no larger than 1.45.

3. A paranasal sinus access implant device for implantation in a human to fluidly connect a lacrimal apparatus to a paranasal sinus through a fistula formed between the lacrimal apparatus and the paranasal sinus, the implant device comprising:
a proximal end at a first longitudinal end of the device to be disposed in the lacrimal apparatus when the device is implanted and a distal end at a second longitudinal end of the device to be disposed in the paranasal sinus when the device is implanted;
a length longitudinally along the implant device between the proximal end and the distal end in a range of from 8 millimeters to 50 millimeters;
a conduit, located between the proximal end and distal end, to be disposed through a fistula between the lacrimal apparatus and the paranasal sinus when the device is implanted, the conduit comprising a distal portion to be disposed in the paranasal sinus when the implant device is implanted;
a head located proximal of the conduit, to be disposed in the lacrimal apparatus when the device is implanted; and
an internal passage through the head and the conduit, to provide a fluid communication path between the lacrimal apparatus and the paranasal sinus when the device is implanted, the internal passage having a width through at least a portion of the conduit in a range of from 0.25 millimeter to 5 millimeters;
and wherein:
at least one of the head and the distal portion of the conduit comprises an exposed surface of exposed material, the exposed surface having an average roughness (Ra) in a range of from 1 nanometer to 200 nanometers;
the Ra is in a range of from 1 nanometer to 50 nanometers over a continuous surface area of at least 2 square millimeters on the head; and
the implant device comprises an antimicrobial agent exposed at a said exposed surface, wherein the antimicrobial agent comprises an antimicrobial peptide or a member selected from the group consisting of silver, poly(ethylene oxide), polyethylene glycol and combinations thereof.

4. A method of making a paranasal sinus access implant device, the method comprising:
providing a preliminary form made of a first material and including a preliminary head structure and a preliminary conduit structure; and
forming a skin portion including at least one second material, the skin portion supported by one or both of the preliminary head structure and the preliminary conduit structure, wherein:
the skin portion has a depth below the exposed surface in a range of from 10 microns to 200 microns; and
the skin portion comprises an exposed surface of an exposed said second material, the exposed surface having an average roughness (Ra) in a range of from 1 to 35 nanometers;
and wherein the implant device comprises, after the forming:
a proximal end at a first longitudinal end of the device to be disposed in the lacrimal apparatus when the device is implanted and a distal end at a second longitudinal end of the device to be disposed in the paranasal sinus when the device is implanted;
a length longitudinally along the implant device between the proximal end and the distal end in a range of from 8 millimeters to 50 millimeters;
a conduit, including the preliminary conduit structure, located between the proximal end and distal end, to be disposed through a fistula between the lacrimal apparatus and the paranasal sinus when the device is implanted, the conduit comprising a distal portion to be disposed in the paranasal sinus when the implant device is implanted;

a head, including the preliminary head structure, located proximal of the conduit, to be disposed in the lacrimal apparatus when the device is implanted;

an internal passage through the head and the conduit, to provide a fluid communication path between the lacrimal apparatus and the paranasal sinus when the device is implanted, the internal passage having a width through at least a portion of the conduit in a range of from 0.25 millimeter to 5 millimeters; and the skin portion with the said exposed surface of an exposed said second material on one or both of the head and the conduit.

\* \* \* \* \*